(12) United States Patent
Choolani et al.

(10) Patent No.: US 8,551,712 B2
(45) Date of Patent: Oct. 8, 2013

(54) DIAGNOSTIC BIOMOLECULE(S)

(76) Inventors: Mahesh Arjandas Choolani, Singapore (SG); Khalil Razvi B M Jabarullah Khan, Loyang (SG); Loganath Annamalai, Singapore (SG); Arijit Biswas, Singapore (SG); Changqing Zhao, Singapore (SG)

( * ) Notice: Subject to any disclaimer, the term of this patent is extended or adjusted under 35 U.S.C. 154(b) by 217 days.

(21) Appl. No.: 12/440,004

(22) PCT Filed: Aug. 20, 2007

(86) PCT No.: PCT/SG2007/000264
§ 371 (c)(1),
(2), (4) Date: Mar. 4, 2009

(87) PCT Pub. No.: WO2008/030186
PCT Pub. Date: Mar. 13, 2008

(65) Prior Publication Data
US 2010/0158916 A1 Jun. 24, 2010

(30) Foreign Application Priority Data
Sep. 5, 2006 (SG) .................................. 200605961

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS

2010/0105067 A1* 4/2010 Fung et al. ...................... 435/7.1

OTHER PUBLICATIONS

Darai et al (Human Reproduction, 2003, 18(8): 1681-1685).*
Daskalakis et al (Eur J Gynec Oncol, 2004, XXV(5): 594-596).*
Pinto et al (Diagn Cytopathol, 1990, 6(3): Abstract).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Tockman et al (Cancer Res., 1992, 52:2711s-2718s).*
Mettler et al (Cancer, 1972, 29: 165-170).*
Ahmed et al., "Proteomic-based *identification* of Haptoglobin-1 Precursor as a Novel Circulating Biomarker of Ovarian Cancer", *British Journal of Cancer*, vol. 91(1):129-140, 2004.
Boss et al., "Clinical Value of Components of the Plasminogen Activation System in Ovarian Cyst Fluid", *Anticancer Research*, vol. 22(1A):275-282, 2002 (Abstract attached for clarity).
Bowman B.H. and Kurosky A., "Haptoglobin: The Evolutionary Product of Duplication, Unequal Crossing Over, and Point Mutation", *Advances in Human Genetics*, vol. 12: Chp, 3, 189-261; and Addendum 453-454, 1982.
Bradford M.M., "A Rapid and Sensitive Method for the Quantitation of Microgram Quantities of Protein Utilizing the Principle of Protein-Dye Binding", *Analytical Biochemistry*, vol. 72:248-254, 1976.
Canis et al., "Frozen Section in Laparoscopic Management of Macroscopically Suspicious Ovarian Masses", *The Journal of the American Association of Gynecologic Laparoscopists*, vol. 11(3):365-369, Aug. 2004.
Cannistra S.A., "Cancer of the Ovary", *The New England Journal of Medicine*, vol. 329(21):1550-1559, 1993.
Darai et al., "Serum and Cyst Fluid Levels of Interleukin (IL) -6, IL-8 and Tumour Necrosis Factor-Alpha in Women with Endometriomas and Benign and Malignant Cystic Ovarian Tumours," *Human Reproduction*, vol. 18(8):1681-1685, 2003.
Daskalakis et al., "Assessment of Ovarian Tumors using Transvaginal Color Doppler Ultrasonography", *European Journal of Gynaecology and Oncology*, vol. 25(5):594-596, 2004.
Devarbhavi et al., "Cancer Antigen 125 in Patients With Chronic Liver Disease", *Mayo Clinic Proceedings*, vol. 77(6):538-541, 2002.
Elg et al., "Ascites Levels of Haptoglobin in Patients with Ovarian Cancer", *Cancer*, vol. 71(12):3938-3941, Jun. 15, 1993.
Guidelines for Referral to a Gynecologic Oncologist: Rationale and Benefits. The Society of Gynecologic Oncologists, *Gynecol Oncol*; 78(3 Pt 2):S1-13, 2000.
Jacobs I.J. and Menon U., "Progress and Challenges in Screening for Early Detection of Ovarian Cancer", *Molecular & Cellular Proteomics*, vol. 3(4):355-366, 2004.
Jacobs et al., "Screening for Ovarian Cancer: a Pilot Randomised Controlled Trial", *The Lancet*, 10 vol. 353(9160):1207-1210, Apr. 1999.
Jennings T.S. and Dottino P.R., "The application of Operative Laparoscopy to Gynecologic Oncology", *Current Opinion in Obstetrics and Gynecology*, vol. 6(1):80-85, 1994.
Karlan et al., "Peritoneal Serous Papillary Carcinoma, a Phenotypic Variant of Familial Ovarian Cancer: Implications for Ovarian Cancer Screening," *American Journal of Obstetrics and Gynecology*, vol. 180(4):917-928, 1999.
Kristensen G.B. and Trope C., "Epithelial Ovarian Carcinoma", *The Lancet*, vol. 349(9045):113-117, Jan. 11, 1997.
Langlois M.R. and Delanghe J.R., "Biological and Clinical Significance of Haptoglobin Polymorphism in Humans", *Clinical Chemistry*, vol. 42(10):1589-1600, 1996.
Lim et al., "Pre and Intraoperative Diagnosis of Ovarian Tumours: How Accurate Are We?" *Australian and New Zealand Journal of Obstetrics and Gynaecology*, vol. 37(2):223-227, May 1997.
Mackey S.E. and Creasman W.T., "Ovarian Cancer Screening", *Journal of Clinical Oncology*, vol. 13(3):783-793, Mar. 1995.

(Continued)

*Primary Examiner* — Sean Aeder
(74) *Attorney, Agent, or Firm* — Clark & Elbing LLP

(57) ABSTRACT

The present invention relates to methods for the identification and/or quantification of biomolecule(s). There is also provided a novel method of identifying and/or quantitating biomolecule(s) in a proliferative cell disorder by providing at least one cyst fluid sample and determining the expression of haptoglobin protein, derivative, mutant and/or fragment thereof.

15 Claims, 9 Drawing Sheets

(56) References Cited

OTHER PUBLICATIONS

Maiman et al., "Laparoscopic Excision of Ovarian Neoplasms Subsequently Found to be Malignant", Society of Gynecologists Oncologists—Abstract 9:170 1991.

Michel et al., "Extensive Cytoreductive Surgery in Advanced Ovarian Carcinoma," *European Journal of Gynaecology and Oncology*, vol. 18(1):9-15, 1997.

Mor et al., "Serum Protein Markers for Early Detection of Ovarian Cancer", *Proceedings of the National Academy of Sciences*, vol. 102(21):7677-7682, May 24, 2005.

Mortz et al., "Identification of Proteins in Polyacrylamide Gels by Mass Spectrometric Peptide Mapping Combined with Database Search", *Biological Mass Spectrometry*, vol. 23. (5):249-261, 1994.

Robinson et al., "Operative Staging and Conservative Surgery in the Management of Low Malignant Potential Ovarian Tumors", *International Journal of Gynecological Cancer*, vol. 2:113-118, 1992.

Vergote et al., "Neoadjuvant Chemotherapy or Primary Debulking Surgery in Advanced Ovarian Carcinoma: A Retrospective Analysis of 285 Patients", *Gynecologic Oncology*, vol. 71: 431-436, 1998.

Wingo et al., "Cancer Incidence and Mortality,1973-1995: A Report Card for the U.S." Cancer, vol. 82, 1197-1207, 1998.

Woolas et al., "Ovarian Cancer Identified Through Screening with Serum Markers But Not by Pelvic Imaging", *International Journal of Gynecological Cancer*, vol. 9(6):497-501, 1999.

Ye et al., "Haptoglobin-$\alpha$ Subunit as Potential Serum Biomarker in Ovarian Cancer: Identification and Characterization Using Proteomic *Profiling* and Mass Spectrometry," Clinical Cancer Research, vol. 9(8):2904-2911, 2003.

Yeo et al., "The Accuracy of Intraoperative Frozen Section in the Diagnosis of Ovarian Tumors," *Journal of Obstetrics and Gynaecology*, vol. 24(3):189-195, 1998.

Zhang et al., "Mining Biomarkers in Human Sera using Proteomic Tools" *Proteomics*, vol. 4(1):244-256, 2004.

Dobryszycka et al., "Biochemical Studies of Cancer Patients Treated with Acridine Derivative (C-283). IV. Changes in the Levels of Serum Haptoglobin and Sialic Acid," Archivum Immunologiae Et Therapiae Experimentals 21:271-279 (1973).

Warwas et al., "Haptoglobin and Proteinase Inhibitors in the Blood Serum of Women with Inflammatory Benign and Neoplastic Lesions of the Ovary," Neoplasma (Bratislave) 33:79-84 (1986).

\* cited by examiner

A

B

DIAGNOSTIC BIOMOLECULE(S)

This application is the U.S. National Stage of International Application No. PCT/SG2007/000264, filed Aug. 20, 2007, which in turn claims the benefit of Singapore Application No. 200605961-2, filed Sep. 5, 2006.

FIELD OF THE INVENTION

The present invention relates to biomolecules. In particular, the present invention relates to diagnostic biomolecules for proliferative cell disorder(s).

BACKGROUND OF THE INVENTION

Epithelial ovarian cancer is the most lethal of the female genital tract cancers. The majority of early-stage cancers are asymptomatic, and over three-quarters of the diagnoses are usually made at a time when the disease is often incurable because regional or distant metastasis has already been established (Wingo et al, 1998). Owing to paucity of symptoms and their insidious onset, most patients present with advanced disease with five-year survival rates being a mere 30% (Kristensen et al, 1997).

Regular pelvic examinations and CA-125 biomarker measurements followed by radiological diagnosis on an individualized basis have been the current practice for detection of this enigmatic condition. Although current early detection protocols have generally involved a combination of ultrasound and serum CA-125 levels, these protocols have met with limited success (Karlan et al., 1999). The largest randomized screening trial to date, which evaluated more than 20,000 women indicated a survival benefit, however, this did not translate into fewer deaths between the screened and unscreened groups of women (Jacobs et al., 1999).

Moreover, CA-125 concentrations are elevated in women with benign gynaecologic conditions including ovarian cysts, endometriosis and uterine fibroids which form part of the differential diagnosis for ovarian cancer (Mackey et al., 1995). Also, women with hepatic disease, renal failure, pancreatitis and other conditions may have elevated CA-125, thus limiting the role of this protein as a marker for ovarian cancer (Devarbhavi et al., 2002). Screening with additional serum markers including CA-19-9 and lysophosphatidic acid as adjuncts to CA-125 screening has also not been shown to be clinically relevant for diagnostic purposes (Woolas et al., 1999).

Most women with ovarian cancers are asymptomatic during the early stages of this disease, and most women present in FIGO (International Federation of Gynecology and Obstetrics) stages III and IV. The currently accepted management for advanced stage ovarian cancer is primary debulking surgery in order to achieve an optimal cytoreduction (defined as residual tumour less than 2 cm) followed by chemotherapy. The surgery usually involves total abdominal hysterectomy, bilateral salpingo-oophorectomy, omentectomy, and pelvic and para-aortic lymphadenectomy. Despite cytoreductive surgery, morbidity and mortality rates remain high with minimal impact on survival rates (Michel et al., 1997; Vergote et al., 1998). In contrast, early stage disease is associated with up to 95% survival (Cannistra, 2004) and a fertility sparing surgical approach can be used in patients who desire fertility preservation (Robinson et al., 1992).

Advances in laparoscopy have allowed gynecologists to perform procedures previously accomplished only by laparotomy. Currently gynecologists perform laparoscopic procedures for treatment of benign ovarian cysts and occasionally encounter unexpected malignancies (Maiman et al., 1991). Inappropriate surgery due to missed diagnosis is associated with poor patient outcome. It is therefore important that an accurate intra-operative diagnosis of malignancy is made for appropriate surgical and therapeutic intervention.

The current state-of-the-art for intraoperative diagnosis is frozen section biopsy (Yeo et al., 1998). This is an expensive, resource and labour intensive test that is not available in many hospitals around the world, and even where available is usually a limited service during office hours. Its accuracy has been quoted from 100% (Lim et al, 1997) to a low of 88.7% (Canis et al., 2004). A reliable, cheaper and more readily available alternative that could be made available to most hospitals is needed.

As such, a method that solves or at least alleviates the problems and limitations of the prior art will be welcome.

SUMMARY OF THE INVENTION

The present invention addresses the problems above and provides methods of identifying and/or quantitating biomolecules. In particular, there is provided a method of identifying and/or quantitating biomarkers. In general, the present invention provides new methods of detecting and/or quantitating proliferative cell disorder(s).

In particular, the present inventors have surprisingly found that the presence and/or expression of haptoglobin protein, derivative, mutant and/or fragment thereof, from at least one cyst fluid sample, may be used as biomarker for detecting and/or quantitating the presence of, or predisposition to, and/or severity of a proliferative cell disorder in a subject.

An assay for determining the level of haptoglobin protein was disclosed in U.S. Pat. No. 6,451,550. However, no suggestion and/or indication regarding the use of this assay associated with cyst fluid samples, and/or for the detection and/or quantitation of a proliferative cell disorder was given.

According to one aspect, the present invention provides a method of detecting and/or quantitating the presence of, or predisposition to, and/or severity of a proliferative cell disorder in a subject, the method comprising:
  (a) providing at least one cyst fluid sample from a subject;
  (b) determining the expression of haptoglobin protein, derivative, mutant and/or fragment thereof; and
  (c) comparing the expression of the haptoglobin protein, derivative, mutant and/or fragment thereof with that of a control, a difference in expression indicating the presence of, or predisposition to, and/or severity of a proliferative cell disorder in the subject.

There is also provided a method of prognosticating the outcome of a cell proliferative cell disorder in a subject, the method comprising:
  (a) providing at least one cyst fluid sample from a subject;
  (b) determining the expression of haptoglobin protein, derivative, mutant and/or fragment thereof; and
  (c) comparing the expression of the haptoglobin protein, derivative, mutant and/or fragment thereof with that of at least one control, a difference in expression indicating the prognosis of a proliferative cell disorder in the subject.

There is also provided a method of selecting at least one candidate for clinical trial(s), experimentation and/or diagnostic test, comprising:
  (a) providing at least one cyst fluid sample from a subject;
  (b) determining the expression of haptoglobin protein, derivative, mutant and/or fragment thereof; and
  (c) comparing the expression of the haptoglobin protein, derivative, mutant and/or fragment thereof with that of at least one control, a difference in expression indicating the suitability of the subject as a candidate.

There is also provided a method of monitoring the efficacy of a treatment for a proliferative cell disorder in a subject, the method comprising:
(a) providing at least two cyst fluid samples from a subject, each sample obtained at different time points;
(b) determining the expression of a haptoglobin protein, derivative, mutant and/or fragment thereof; and
(c) comparing the expression of the haptoglobin protein, derivative, mutant and/or fragment thereof in the at least two samples, a difference in expression indicating the efficacy of treatment in the subject.

The cyst fluid samples may be obtained from ovarian cysts.

The control is at least one subject not diagnosed with the cell proliferative disorder or the control may be a reference subject, experiment or value by which values obtained in samples or tests can be compared against. The haptoglobin protein, derivative, mutant and/or fragment may be human haptoglobin protein, derivative, mutant and/or fragment thereof. The proliferative cell disorder may be a cancer; in particular, ovarian cancer.

The sequence of the haptoglobin protein is given in SEQ ID NO:2. The determining may be by colorimetry. The colorimetry may be based on peroxidase activity of a hemoglobin-haptoglobin complex on a substrate. The determining may be by Mass Spectrometry. The Mass Spectrometry may be Matrix Assisted Laser Desorption/Ionization-Time of Flight Mass Spectrometry. The determining may be by an immuno-reactive assay. The immuno-reactive assay may be Enzyme-Linked Immunosorbent Assay. The method may further comprise at least one CA-125 measurement on the sample(s) and/or at least one ultrasound evaluation of the subject.

There is also provided a method of treating a proliferative cell disorder in a subject, the method comprising varying the expression of a haptoglobin protein, derivative, mutant and/or fragment thereof, or gene, gene transcript, RNA, derivative and/or mutation thereof.

The haptoglobin protein may have the amino acid sequence of SEQ ID NO:2. The varying may be obtained by administering to the subject a polypeptide binding to all or part of the amino acid sequence of the haptoglobin protein, derivative, mutant and/or fragment thereof. The binding polypeptide may be an antibody.

The haptoglobin gene may have the DNA sequence of SEQ ID NO:1. The varying may be obtained by administering to a subject a nucleic acid binding to all or part of the haptoglobin gene, gene transcript, RNA, derivative and/or mutation thereof. The nucleic acid may be DNA or RNA. The nucleic acid may be siRNA.

The varying may be obtained by administering a compound complementary to all or part of the DNA sequence given in SEQ ID NO:1. The varying may comprise reducing the expression of the haptoglobin protein, derivative, mutant and/or fragment thereof, or gene, gene transcript, RNA, derivative and/or mutation thereof.

There is also provided a diagnostic and/or prognositic kit for the diagnosis and/or prognostic evaluation of a cell proliferative disorder in a subject, the diagnostic and/or prognositic kit comprising at least one molecule or compound binding and/or reacting to a haptoglobin protein, derivative, mutant and/or fragment thereof obtained from a cyst fluid sample.

There is also provided a kit for treating a proliferative cell disorder in a subject, the kit comprising at least one molecule or compound reacting to haptoglobin gene, gene transcript, RNA, derivative and/or mutation thereof; and/or binding to haptoglobin protein, derivative, mutant and/or fragment thereof obtained from a cyst fluid sample.

The molecule may be a polypeptide binding to the haptoglobin protein, derivative, mutant and/or fragment thereof. The molecule may be an antibody binding to the haptoglobin protein, derivative, mutant and/or fragment thereof. The molecule may be a substrate of haptoglobin and the reacting may be an enzymatic action by the haptoglobin protein, derivative, mutant and/or fragment thereof.

The subject may be a mammal; in particular, a human. The proliferative cell disorder may be a cancer; in particular, ovarian cancer.

DETAILED DESCRIPTION

Figure 1:
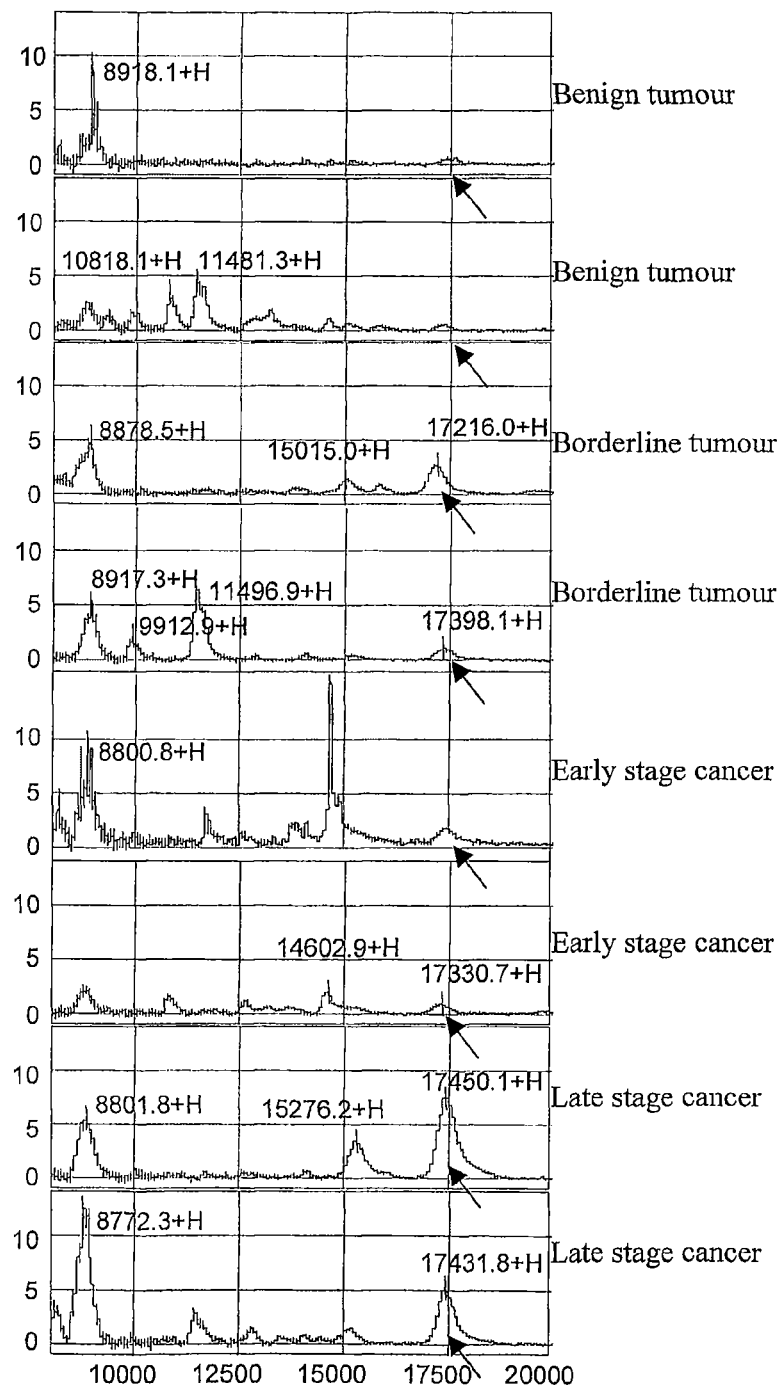
FIG. 1. Representative SELDI-TOF protein profiles in cystic fluid proteins between 8-20 kDa according to m/z ratio using NP20 protein chips. Relative peak intensities were normalized to total ion current for the entire data set. Arrow indicates the position of the 17 kDa peak observed in ovarian carcinomas but this peak is less frequently observed in benign tumours.

Bibliographic references mentioned in the present specification are for convenience listed in the form of a list of references and added at the end of the examples. The whole content of such bibliographic references is herein incorporated by reference.

DEFINITIONS

Biomolecule—A biological molecule such as amino acid, peptide, protein, nucleic acid (DNA and/or RNA), lipid, carbohydrate, and their derivatives.

Biomarker—Biomarkers are biochemicals or biomolecules (proteins, polypeptides, carbohydrates, lipids, etc, and their derivatives) associated with the presence and severity of specific disease states or different treatment conditions. The biomolecule may be a wild-type molecule, or a mutant, a derivative and/or a fragment thereof. For the purpose of the present invention a mutant, derivative and/or a fragment thereof means a biomolecule which possesses or share characteristics such as structure and/or biological activity similar to or which may be correlated or comparable to that of the wild type molecule. According to the present invention, a protein or protein derivative may be used as a biomarker. Biomarkers are detectable and measurable by a variety of methods. To identify a biomarker, it is usually necessary to detect a difference or change in the expression or abundance of a biological molecule and identifying the particular molecule changed.

Expression or abundance of a biomarker—the expression of a biomarker may be determined from the presence or abundance of its gene, gene transcript, and gene product. The terms "gene" and "gene transcript" include RNA sequences complementary to the gene and cDNA sequences obtained by reverse transcription of the gene transcript. The terms also include the wild type gene, variations and mutations of the gene and gene transcript wherein the variation or mutation share substantial identity with the gene or gene transcript. Similarly, "gene product" includes wild type gene product, variations, fragments or derivatives thereof. "Substantial identity" means that the variants of the gene or gene product retain sufficient identity for them to be detectable by methods and probes used for the wild type gene or gene product and retain the same functions as the wild type gene or gene products. The determination may be qualitative such as whether the biomarker is expressed, or the determination may be quantitative, or the determination may be semi-quantitative by any method known in the art such as by microarray technology, polymerase chain reaction or colorimetric method. Departure (increase or decrease) from normal levels in the non-diseased state can indicate a disease state or predisposition to a disease state. For example, the overexpression or increased abundance of a protein may be indicative of a disease state, the severity of the disease state and hence the prognosis for the subject in which the biomarker was determined, and/or it might be an indicator of susceptibility to a disease state. The difference in expression and abundance may be determined between different biomarkers or between the same biomarker under different conditions or time points. The expression of the biomarker(s) may then be compared and correlated to a reference value or to other values obtained at different time points or between different biomarkers to determine the correlation with the presence, severity of a disease state, to determine the efficacy of a treatment, or to determine a prognosis of the disease outcome for the subject. Reference values may be determined from a statistically significant number of subjects suffering from or not suffering from the disease. The expression of the biomarker(s) may also be used in conjunction with other suitable diagnostic or prognostic markers, biomarkers or indices to obtain a higher level of confidence. When a biomarker is said to be "over expressed" when compared to controls, it is meant that the expression of that biomarker is at an abundance or level that is statistically significantly more than that naturally expressed by at least one wild type or non-mutant control subject not diagnosed with the disease state or condition. Similarly, when a biomarker is "under expressed", the expression of that biomarker is statistically significantly less than that naturally expressed by at least one wild type or non-mutant control subject not diagnosed with the disease state or condition. Under this definition, a subject genetically deficient for that biomarker cannot be said to be under expressing that biomarker. Similarly, when transfected with the gene for that biomarker so that that biomarker is expressed, the deficient subject cannot be said to be over expressing the biomarker as he was originally deficient in that biomarker.

Control—A reference subject, experiment or value by which values obtained in tests can be compared against. Control values or ranges usually represent the "normal" state so that a statistically difference or deviation of the control values or ranges represents an abnormal or disease state. A person skilled in the art will know how to select and/or obtain control subjects, experiments or values for use as references.

Selecting a subject or candidate—to determine the suitability of a subject or candidate for a clinical trial, experimentation, diagnostic and/or other tests by measuring at least one characteristic of the subject or candidate. The value representing the characteristic is then compared to a reference or control value or range of values, and the result is used to determine if the subject or candidate is suitable for the trial, experimentation, diagnostic and/or other test. A person skilled in the art will know how to select subjects or candidates based on their amenability to a particular treatment, or their susceptibility to a particular challenge or disease.

Cancer—A malignant and uncontrolled growth of cells in one part of the body that can spread to other parts of the body.

Cyst fluid—A cyst is a fluid-filled sac that can be located anywhere in the body. The fluid it contains is cyst fluid.

Nucleic acid—"Nucleic acids" are linear polymers of nucleotides, linked by 3', 5' phosphodiester linkages. In DNA, deoxyribonucleic acid, the sugar group is deoxyribose and the bases of the nucleotides adenine, guanine, thymine and cytosine. RNA or ribonucleic acid, has ribose as the sugar and uracil replaces thymine. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The invention also features an isolated nucleic acid at least 50% (including any percentage between 50% and 100%, e.g., 85%, 95%, or 100%) identical to SEQ ID NO: 1, which can be used, e.g., for detection of the human haptoglobin gene in a subject, or screening of therapeutic compounds for treating a cell proliferation-associated disorder.

Gene product—According to the present invention, the gene product refers to a gene product other than a protein. The gene product may be a length of RNA with a biological functional other than a gene transcript coded for by a particular gene.

Gene transcript—the messenger RNA sequence coded for by a gene.

Protein—A biological molecule composed of one or more chains of amino acids in a specific order. Proteins may have derivatives such as isoforms. A protein isoform is a version of a protein with some small differences, usually a splice variant or the product of some post-translational modification. According to the present invention, besides isoforms, a protein also encompasses fragments that are sufficiently large enough for the protein to be detected, identified and/or quantified by the method(s) used. A protein complex is a mixture of different proteins. The expression of proteins may be affected or influenced by a drug. Such proteins are called drug-responsive proteins. The invention also features an isolated protein at least 50% (including any percentage between 50% and 100%, e.g., 85%, 95%, or 100%) identical to SEQ ID NO: 2, which can be used, e.g., for detection of the human haptoglobin protein in a subject, or screening of therapeutic compounds for treating a cell proliferation-associated disorder.

Proteome—The set of proteins expressed by a cell or organ at a particular time and under specific conditions. Accordingly, proteomic analysis is the study of the full set of proteins encoded by a genome.

Percentage Identity—The "percent identity" of two nucleic acid sequences is determined using the algorithm of Karlin and Altschul (1990), modified as in Karlin and Altschul (1993). Such an algorithm is incorporated into the XBLAST programs of Altschul et al. (1990). BLAST nucleic acid searches are performed with the XBLAST program. Where gaps exist between two sequences, Gapped BLAST is utilized as described in Altschul et al. (1997). When utilizing BLAST and Gapped BLAST programs, the default parameters of the respective programs (e.g., XBLAST) are used. See the World Wide Web address ncbi.nlm.nih.gov. The percentage identity of other sequences such as protein sequences may similarly be determined.

Antibody—An immunoglobulin protein produced by B-lymphocytes of the immune system that binds to a specific antigen molecule. The term includes monoclonal antibodies, polyclonal antibodies as well as fragments thereof, such as Fab, F(ab')$_2$, and Fv fragments.

Drug—any compound used for the treatment (amelioration of, reduction of, or cure for) any disease or pathological state or condition.

Screening—to select a compound that has an effect in any disease or pathological condition. Screening may involve detecting, identifying and/or quantifying any biomolecule such as a protein, the expression of which is affected by the compound.

Treating—the administration of a composition to a subject, who has a cell proliferation-associated disorder, with the purpose to cure, alleviate, relieve, remedy, prevent, or ameliorate the disorder, the symptom of the disorder, the disease state secondary to the disorder, or the predisposition toward the disorder. An "effective amount" is an amount of the composition that is capable of producing a medically desirable result, e.g., as described above, in a treated subject. This method can be performed alone or in conjunction with other drugs or therapy.

Hybridizing, hybridisable—a biomolecule such as a sequence of nucleic acids may hybridize to another sequence of nucleic acids if there are sufficient stretches of complementary nucleotides between them. For peptides and proteins, one protein such as an antibody or fragment thereof may hybridize to another protein if there are sufficient complementary or recognition structures between these two biomolecules.

The present invention provides methods for identifying and/or quantitating biomolecules. In particular, there is provided a method of identifying and/or quantitating biomarkers. In general, the present invention provides new methods of detecting and/or quantitating proliferative cell disorder(s).

According to one aspect, the present invention provides a method of detecting and/or quantitating the presence of, or predisposition to, and/or severity of a proliferative cell disorder in a subject, the method comprising:
 (a) providing at least one cyst fluid sample from a subject;
 (b) determining the expression of haptoglobin protein, derivative, mutant and/or fragment thereof; and
 (c) comparing the expression of the haptoglobin protein, derivative, mutant and/or fragment thereof with that of a control, a difference in expression indicating the presence of, or predisposition to, and/or severity of a proliferative cell disorder in the subject.

There is also provided a method of prognosticating the outcome of a cell proliferative cell disorder in a subject, the method comprising:
 (a) providing at least one cyst fluid sample from a subject;
 (b) determining the expression of haptoglobin protein, derivative, mutant and/or fragment thereof; and
 (c) comparing the expression of the haptoglobin protein, derivative, mutant and/or fragment thereof with that of at least one control, a difference in expression indicating the prognosis of a proliferative cell disorder in the subject.

There is also provided a method of selecting at least one candidate for clinical trial(s), experimentation and/or diagnostic test, comprising:
 (a) providing at least one cyst fluid sample from a subject;
 (b) determining the expression of haptoglobin protein, derivative, mutant and/or fragment thereof; and
 (c) comparing the expression of the haptoglobin protein, derivative, mutant and/or fragment thereof with that of at least one control, a difference in expression indicating the suitability of the subject as a candidate.

There is also provided a method of monitoring the efficacy of a treatment for a proliferative cell disorder in a subject, the method comprising:
 (a) providing at least two cyst fluid samples from a subject, each sample obtained at different time points;
 (b) determining the expression of a haptoglobin protein, derivative, mutant and/or fragment thereof; and
 (d) comparing the expression of the haptoglobin protein, derivative, mutant and/or fragment thereof in the at least two samples, a difference in expression indicating the efficacy of treatment in the subject.

The control may be at least one subject not diagnosed with the cell proliferative disorder. The control may also be a reference subject, experiment or value by which values obtained in tests can be compared against. Control values or ranges usually represent the "normal" state so that a statistical difference or deviation of the control values or ranges represent an abnormal or disease state. The haptoglobin protein, derivative, mutant and/or fragment may be human haptoglobin protein, derivative, mutant and/or fragment thereof. The proliferative cell disorder may be a cancer; in particular, ovarian cancer.

The sequence of the haptoglobin protein is given in SEQ ID NO:2. The determining may be by colorimetry. The colorimetry may be based on peroxidase activity of a hemoglobin-haptoglobin complex on a substrate. The determining may be by Mass Spectrometry. The Mass Spectrometry may be Matrix Assisted Laser Desorption/Ionization-Time of Flight Mass Spectrometry. The determining may be by an immuno-reactive assay. The immuno-reactive assay may be Enzyme-Linked Immunosorbent Assay. The method may further comprise at least one CA-125 measurement on the sample(s) and/or at least one ultrasound evaluation of the subject.

There is also provided a method of treating a proliferative cell disorder in a subject, the method comprising varying the expression of a haptoglobin protein, derivative, mutant and/or fragment thereof, or gene, gene transcript, RNA, derivative and/or mutation thereof.

The haptoglobin protein may have the amino acid sequence of SEQ ID NO:2. The varying may be obtained by administering to the subject a polypeptide binding to all or part of the amino acid sequence of the haptoglobin protein, derivative, mutant and/or fragment thereof. The binding polypeptide may be an antibody.

The haptoglobin gene may have the DNA sequence of SEQ ID NO:1. The varying may be obtained by administering to a subject a nucleic acid binding to all or part of the haptoglobin gene, gene transcript, RNA, derivative and/or mutation thereof. The nucleic acid may be DNA or RNA. The nucleic acid may be siRNA.

The varying may be obtained by administering a compound complementary to all or part of the DNA sequence given in SEQ ID NO:1. The varying may comprise reducing the expression of the haptoglobin protein, derivative, mutant and/or fragment thereof, or gene, gene transcript, RNA, derivative and/or mutation thereof.

There is also provided a diagnostic and/or prognostic kit for the diagnosis and/or prognostic evaluation of a cell proliferative disorder in a subject, the diagnostic, prognostic and/or predictive kit comprising at least one molecule or compound binding and/or reacting to a haptoglobin protein, derivative, mutant and/or fragment thereof obtained from a cyst fluid sample.

There is also provided a kit for treating a proliferative cell disorder in a subject, the kit comprising at least one molecule or compound reacting to haptoglobin gene, gene transcript, RNA, derivative and/or mutation thereof; and/or binding to haptoglobin protein, derivative, mutant and/or fragment thereof obtained from a cyst fluid sample.

The molecule may be at least one polypeptide binding to the haptoglobin protein, derivative, mutant and/or fragment thereof. The molecule may be an antibody binding to the haptoglobin protein, derivative, mutant and/or fragment thereof. The molecule may be a substrate of haptoglobin and the reacting may be an enzymatic action by the haptoglobin protein, derivative, mutant and/or fragment thereof.

The subject may be a mammal; in particular, a human. The proliferative cell disorder may be a cancer; in particular, an ovarian cancer.

Given the current understanding about the steep survival gradient relative to the stage at which this cancer is diagnosed, it is proposed that early detection remains the most promising approach to improve the long-term survival rates for ovarian cancer. Knowledge of the early developmental stages of ovarian cancer at the cellular and molecular levels is important since altered protein expression is a hallmark of neoplastic change. Therefore, proteins secreted by ovarian cancer cells into cyst fluid may prove to be useful markers for intra-operative discrimination of cancer from benign cysts. They may also provide a richer source of potential tumour markers which are more difficult to isolate and identify when diluted amongst more abundant proteins in the large circulating blood volume. Cancer tumour markers is an area where the focus of proteomic research is the target of current investigation.

Elevated levels of CA125, CA19-9, vascular endothelial growth factor (VEGF), interleukin 6 (IL-6), IL-8 and tumour necrosis factor (TNF) have been observed in ascitic fluid from these tumour patients (Darai et al., 2003) In addition, significant concentrations in the markers of plasminogen activation system including uPA, PAI-1 and the ratio of uPA:PAI-1, tPA:PAI-1 in cyst fluid from ovarian tumours have been reported in these patients (Boss et al., 2002). However, there is no teaching or suggestion that haptoglobin in cyst fluid may be useful as a diagnostic biomarker for a cell proliferative disorder.

Investigations were carried out to detect potential biomarkers for early diagnosis of epithelial ovarian cancer using the proteomics-based approach from cyst fluid of ovarian tumor.

In order to obtain further insight into the biochemical mechanism of neoplastic processes, proteomics-based approaches have been applied to medical application and diagnosis. High-throughput proteomics technology is a new and emerging field of protein science which complements conventional one- or two-dimensional gel electrophoresis. In this regard, the recent SELDI technique may be employed to separate and fractionate proteins, followed by identification of these specific proteins by mass spectrometry (MS) (Zhang et al., 2004) in an attempt to characterize potential biomarkers in biological fluids.

By investigating differences in protein expression between benign and malignant ovarian tumours in ovarian cyst fluid, it may be possible to detect proteins that are related to malignancy but not to benign diseases of the ovary. We employed a number of methodologies to identify changes in protein expression under the method of the present invention.

In one embodiment in this study, we used SELDI (Surface Enhanced Laser Desorption/Ionization Time of Flight), SDS-PAGE (sodium dodecyl sulphate polyacrylamide gel electrophoresis), western blotting analysis, tandem MALDI-TOF-MS/MS (matrix assisted laser desorption/ionization time-of-flight tandem mass spectrometry) techniques and immuno-reactive assays such as quantitative ELISA (enzyme-linked immunosorbent assay). We were able to establish the first evidence for haptoglobin as a potential biomarker in cyst fluid which differentiates ovarian cancer from benign ovarian tumours.

Sixty-three cases of cyst fluid (28 from malignant epithelial ovarian tumours and 35 from benign epithelial ovarian tumours) were collected and processed for SELDI-TOF mass spectrometry analysis. SDS-PAGE and MALDI-TOF-MS-MS followed by database search using MASCOT were used to identify the potential protein marker.

Western blotting technique and immunocapture assays were performed to confirm the identity of haptoglobin. A sandwich ELISA method as described in Example 5 was also developed to compare the levels of this protein in cyst fluid from epithelial ovarian cancer and benign tumour. In addition, to introduce clinical relevance and suitability for rapid screening (ca. 5 min), we employed a colorimetric, dye-binding assay to determine the real time identification of this target protein which could facilitate diagnosis of the specific stage of cancer.

Mass spectrometry (MS) separates molecules based on their mass-to-charge (m/z) ratios. In an MS system, molecules of interest are ionized, separated in an analyzer based on their m/z ratios and then detected by a detector. The results may be displayed in the form of an m/z spectrum. The MS system usually includes a data analysis sub-system for the analysis of the data.

Ionization of the molecules may be achieved by any known method in the art. For example, ionization of the molecules may be achieved by the following methods, including: Atmospheric Pressure Chemical Ionisation (APCI), Thermospray Ionisation (TSP), Chemical Ionisation (CI), Electron Impact (EI), Electrospray Ionisation (ESI), Fast Atom Bombardment (FAB), Field Desorption/Field Ionisation (FD/FI), Surface Enhanced Laser Desorption Ionization (SELDI) and Matrix Assisted Laser Desorption Ionisation (MALDI).

The analyzer may utilize different principles for the analysis of the ions, including quadrupoles, magnetic sectors, and both Fourier transform, quadrupole ion traps and time-of-flight (TOF) analysers. Two or more analyzers may be arranged in tandem. Commonly used tandem geometries include quadrupole-quadrupole, magnetic sector-quadrupole, and quadrupole-time-of-flight geometries.

A person skilled in the art will be able to select different ionization, analysis and/or detection methods to best study a biomolecule of interest such as proteins.

A prognostic method of the present invention involves comparing expression of the biomarker in samples from patients with reference values obtained from one or more patients with known disease outcomes, or from known benign or malignant tissues or cells. Thereafter, it will be possible to determine the prognoses of these patients.

A diagnostic method of the invention involves comparing one or more of the haptoglobin protein and/or nuclei acid levels in a sample prepared from a subject (i.e., an animal or a human) with that in a sample prepared from a normal subject, i.e., a subject who does not suffer from or at risk for developing a cell proliferation-associated disorder or that in a control sample.

For both prognostic and diagnostic methods, a higher haptoglobin level indicates that the subject is suffering from, or at risk for, a cell proliferation-associated disorder. This method may be used on their own or in conjunction with other procedures to diagnose a cell proliferation-associated disorder in appropriate subjects and to provide a prognosis as to the outcome of the disease.

This invention further provides a method for preventing and/or treating a cell proliferation-associated disorder. Subjects to be treated may be identified, for example, by determining the haptoglobin genomic DNA, DNA transcript or DNA product level in at least one sample prepared from at least one subject by methods described above. If the haptoglobin genomic DNA level is higher in the sample from the target subject than from a normal subject, the target subject is a candidate for treatment with an effective amount of compound that decreases the haptoglobin genomic DNA, DNA transcript or DNA product level.

In at least one in vivo approach, a therapeutic composition (e.g., a composition comprising at least one compound identified as described above) is administered to the subject. Generally, the compound will be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally intranasally, intragastrically, intratracheally, or intrapulmonarily. For prevention and treatment of cancer, the compound may be delivered directly to the cancer tissue.

The dosage required depends on the choice of the route of administration; the nature of the formulation; the nature of the subject's illness; the subject's size, weight, surface area, age, and sex; other drugs being administered; and the judgment of an attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels may be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide comprising a nucleic acid sequence encoding an anti-sense haptoglobin RNA can be delivered to the subject, for example, by the use of polymeric, biodegradable microparticle or microcapsule delivery devices known in the art.

Another way to achieve uptake of the nucleic acid is using liposomes, prepared by standard methods. The vectors may be incorporated alone into these delivery vehicles or co-incorporated with tissue-specific antibodies. Alternatively, one may prepare a molecular conjugate composed of a plasmid or other vector attached to poly-L-lysine by electrostatic or covalent forces. Poly-L-lysine binds to a ligand capable of binding to a receptor on target cells. Alternatively, tissue specific targeting may be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding an anti-sense haptoglobin RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer may also be located downstream of the transcription initiation site.

The inhibition of gene expression may be achieved through use of small inhibitory RNA sequences (siRNA). Expression of the haptoglobin gene may also be inhibited using RNA interference (RNAi). This is a technique for post-transcriptional gene silencing ("PTGS"), in which target gene activity is specifically abolished with cognate double-stranded RNA ("dsRNA"). In many embodiments, dsRNA of about 21 nucleotides, homologous to the target gene, is introduced into the cell and a sequence specific reduction in gene activity is observed. RNA interference provides a mechanism of gene silencing at the mRNA level. It offers an efficient and broadly applicable approach for gene knock-out as well as for therapeutic purposes.

Suitable expression vectors for these polynucleotides include plasmids and viral vectors such as herpes viruses, retroviruses, vaccinia viruses, attenuated vaccinia viruses, canary pox viruses, adenoviruses and adeno-associated viruses, among others.

Polynucleotides may be administered in the presence of at least one pharmaceutically acceptable carrier, vehicle, diluent and/or excipient. Pharmaceutically acceptable carriers are biologically compatible vehicles that may be suitable for administration to an animal or a human, e.g., physiological saline or liposomes. A preferred dosage for administration of polynucleotide may be from approximately 106 to 1012 copies of the polynucleotide molecule. This dose may be repeatedly administered, as needed. Routes of administration may be any of those listed above.

Antibodies (monoclonal or polyclonal) to haptoglobin may be used to reduce the level of haptoglobin protein, or to decrease the level of haptoglobin in a subject. The term "antibody" includes intact molecules as well as fragments thereof, such as Fab, F(ab')2, and Fv which are capable of binding to an epitopic determinant present in the haptoglobin protein. Methods of making monoclonal and polyclonal antibodies and fragments thereof are known in the art. See, for example, Harlow and Lane, (1988) Antibodies: A Laboratory Manual, Cold Spring Harbor Laboratory, New York.

Other compounds that may be used to inhibit haptoglobin include a peptide or polypeptide comprising an amino acid sequence at the C-terminus of haptoglobin.

In addition, the invention provides a method of developing a procedure for treating a cell proliferation-associated disorder by providing at least one subject(s) suffering from a cell proliferation-associated disorder (e.g., the subject(s) having amplified haptoglobin genomic DNA); administering to each subject an effective amount of an haptoglobin inhibitor followed by an effective amount of a nucleotide or nucleoside analog (e.g., gemcitabine), each at a unique time point; and selecting an optimal time point at which the cell proliferation-associated disorder is inhibited to the greatest extent. Once the optimal time point has been identified, the procedure may be used to treat a cell proliferation-associated disorder in appropriate subjects.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Having now generally described the invention, the same will be more readily understood through reference to the following examples which are provided by way of illustration, and are not intended to be limiting of the present invention.

While the examples show how the method of the present invention is applied to different treatment conditions, it will be appreciated by one skilled in the art that the method of the present invention may also be used to compare proteomic changes between different disease conditions as well.

Materials and Methods
Patient and Clinical Samples

Women aged 20 to 72 years with malignant (n=28 including 11 early and 17 late stage cancers) and 35 benign epithelial ovarian tumours were recruited for open surgical or laparoscopic treatment in the Department of Obstetrics & Gynecology, National University Hospital, Singapore. Fluids from cyst of ovarian carcinomas and benign tumours were collected during surgery without intraoperative spillage. The fluids were centrifuged at 1500 g for 10 minutes at 4° C. and the supernatants were divided into aliquots of 1 ml and snap frozen in liquid nitrogen. All samples were stored at −80° C. until analysis. The cyst fluid sample collection used for this study was approved by the Domain Specific Review Board, National Healthcare Group, Singapore and informed consent was obtained from each patient.

SELDI-TOF Analysis

SELDI-TOF profiling for hydrophilic cyst fluid proteins was obtained using normal phase (NP20-hydrophilic surface) protein chips (Ciphergen Biosystems, Calif., USA). The protein chips were pre-incubated with 5 µl of Millipure water for 5 minutes. 5 µl of sample was then added to the NP20 protein chip spots and incubated for 1 hour. Immunocapture experiments were performed using a PS20 ProteinChip array (Ciphergen Biosystems, Calif., USA) precoated with anti-haptoglobin antibody. Samples (10 µL) were incubated with 90 µL binding buffer and allowed to bind for 2 hours. After two washes with washing buffer (0.5% Triton X-100 in PBS), the array was air dried and treated with saturated sinapinic acid in 0.5% trifluoroacetic acid and 50% acetonitrile and analyzed using the Ciphergen protein chip Reader (model PBSII; Ciphergen Biosystems, Calif., USA). Triplicate sets were performed for each sample.

The arrays were analyzed with the Ciphergen protein chip reader. The mass spectra of proteins were generated using an average of 80 laser shots at one sample. For data acquisition of low molecular weight proteins, the detection size range was between 8~25 kDa, with a maximum size of 30 kDa. The detector intensity was set at 10, and the laser intensity was set at 240V. For the proteins with the molecular mass range between 25-50 kDa with a maximum size of 60 kDa, the detector sensitivity and laser intensity of 10 and 260V respectively were used. The mass to charge ratio (m/z) of each of the proteins captured on the array surface was determined according to externally calibrated standards (Ciphergen Biosystems, Calif., USA): bovine insulin (5,733.6 Da), human ubiquitin (8,564.8 Da), bovine cytochrome c (12,230.9 Da), equine myoglobin (16,951.5 Da), bovine β-lactoglobulin A (18,363.3 Da) and horse-radish peroxidase (43,240 Da).

The mass spectra obtained from the spectrometer were first processed using Ciphergen protein chip software version 3.0 for baseline correction and peak detection in the auto mode. Baseline subtraction was performed on a spectrum to eliminate any baseline signal that was due mainly to chemical noise caused by Energy Absorbing Molecule (EAM). Peak detection identified areas of the mass spectrum as peaks by comparing the signal to neighbouring valley depth calculations with a signal to noise ratio of more than 5.

Protein Separation and Identification

Cyst fluid protein was concentrated using acetone precipitation method overnight at 4° C. Protein pellets were resuspended in PBS buffer and centrifuged. Protein concentration was estimated using the Bradford method (Bradford, 1976) and an equal quantity of protein (20 µg) was loaded into 15% SDS-PAGE gel. The gel was stained using mass spectrometry compatible silver stain plus kit (Bio-Rad laboratories, Calif., USA). The protein bands were excised and processed for in-gel digestion. The gel bands were cut into small pieces which were then destained, washed and dehydrated. Reduction and alkylation were performed by the addition of dithiothreitol (DTT; 10 mM) and iodacetamide (IAA; 55 mM) (Sigma-Aldrich, Mo., USA) followed by washing and dehydration. The gel pieces were then suspended in 12.5 ng/µl trypsin in 50 mM ammonium bicarbonate. The peptides were extracted and concentrated in vacuo and desalted using Zip-Tip (Millipore, Mass., USA). Peptide identification was carried out using a Tandem Mass Spectrometry Voyager-DE STR MALDI-TOF mass spectrometer (Applied Biosystems, Calif., USA) with the following grid specifications. The MS automatic data acquisition was performed in delayed extraction, reflection mode, with accelerating voltage of 20500 volts; grid voltage, 73.5% grid wire, 0.01% and extraction time of 380 ns. Laser intensity was set at 2700, with 100 shots per spectrum. The mass range was set between 800-3500 Da. The mixture of angiotensin I and ACTH peptides (1296.6835 Da and 2465.1989 Da (M+H+) ions) were set as internal calibration standards.

Conditions for Mascot Database Search:

Database searching was performed with Mascot (http://matrixscience.com). For Mascot searching, parameters were set as follows: Database was chosen with NCBI non-redundant databases and Swissprot, *Homo sapiens*, 0-250 kDa molecular mass, tryptic digest with a maximum number of one missed cleavage. Peptide masses were stated to be monoisotopic, and methionine residues were assumed to be partially oxidized. Additionally, the searches were carried out with carbamidomethylation of cysteine residues. The mass tolerance was set as 100 ppm.

Western Blotting Analysis

To perform Western blotting analysis for haptoglobin, 10 μg of protein from each sample were separated by 15% SDS-PAGE. The bands were then electrically transferred onto 0.45 μm nitrocellulose membranes using Semi-dry Transblot Cell (Bio-Rad laboratories, Calif., USA). Membranes were soaked in 5% non-fat dry milk in TBST (20 mM Tris base; 500 mM NaCl; 0.05% Tween 20; pH 7.5) for 1 hour at room temperature and incubated overnight at 4° C. with rabbit anti-human haptoglobin polyclonal antibody (1:5000) (Dakocytomation, Glostrup, Denmark). They were washed three times with TBST and incubated with a HRP labeled anti-rabbit secondary antibody (Pierce Biotechnology, Ill., USA) diluted in 5% non-fat dry milk in TBST (1:1000) for 1 hour at room temperature. The membranes were then washed and developed with chemiluminescent substrates (Pierce Biotechnology, Ill., USA).

Antibody generation and Quantitative analysis by the sandwich enzyme-linked immunosorbent assay (ELISA) method Polyclonal rabbit antibody against Hp α-subunit was generated using amino acid sequence, CKNYYKL-RTQGDGVY (SEQ ID NO:3) (BioGenes, Berlin, Germany). The affinity-purified antibody developed was then used for the ELISA analysis. The total haptoglobin level or haptoglobin α-subunit was quantified using sandwich ELISA with polyclonal antibodies against Hp or Hp α-subunit. The goat anti-human Hp antibody (Biodesign, Me., USA) in an appropriate dilution (1:200) with 0.5% BSA in PBST buffer (0.05% Tween20 in PBS buffer) was coated onto PVC plates (NUNC, Roskilde, Denmark) overnight at 4° C. After blocking with 200 ul of 3% non-fat dry milk in PBST for 2 hours at room temperature, individual cyst fluid sample was mixed with 0.5% BSA in PBST buffer (1:100). The diluted mixture of 200 μl was added and incubated for 2 hour at room temperature. The purified human haptoglobin (Sigma-Aldrich, Mo., USA) or haptoglobin α-subunit (BioGenes, Berline, Germany) was used as standard.

The plate was then incubated with rabbit anti-human Hp antibody (1:400) (Dakocytomation, Glostrup, Denmark) or Hp α-subunit antibody (1:100) diluted in 0.5% BSA in PBST at room temperature for 2 hours followed by adding biotin-labeled anti-rabbit secondary antibody (1:400) and alkaline phosphatase streptavidin (1:400) (Vector Laboratories, Calif., USA). P-Nitrophenylphosphate (Vector Laboratories, Calif., USA) was applied at 5 mM in 100 mM sodium bicarbonate solution at 37° C. for about 1 hour. To determine the concentration of haptoglobin, the plate was read at 405 nm using ELISA reader (Tecan, Salzburg, Austria). Between each stage of an assay, the plate was washed 4 times by immersion in PBST buffer and then emptying.

Measurement of haptoglobin using the PHASE RANGE Haptoglobin assay kits To determine the effectiveness of accurate and fast method to detect the malignancy of ovarian tumor based on proteins present in cyst fluid haptoglobin assay was conducted in a low pH environment with a commercial PHASE RANGE Haptoglobin assay (Tridelta Development Ltd, Kildare, Ireland; also described in U.S. Pat. No. 6,451,550). Clear cysts were selected for this test and cyst fluid from 20 benign and 14 malignant ovarian tumours was included for this evaluation. The assay is based on the fact that the peroxidase activity of free hemoglobin is inhibited at a low pH environment. Binding of haptoglobin with hemoglobin in a complex will preserve the peroxidase activity of the bound hemoglobin. Hence the peroxidase activity is directly proportional to the amount of haptoglobin present in the specimen. The assay was performed in 96-well plate in accordance with the manufacturer's instruction. In this assay, 7.5 μl of each prepared calibrator (0-2 mg/ml) along with test specimens were transferred in duplicate, to the blank microplate. Then 100 μl of hemoglobin solution was added and thoroughly mixed with sample. 140 μl of a mixture of chromogen and substrate was added and the plate was incubated for 3 and 5 min. Initial tests were conducted and standard color was decided as a cut-off to discriminate malignant from benign cyst. Positive color reaction was recorded at 3 and 5 mins respectively.

Evaluation of Ovarian Tumor Using Ultrasonographic Scoring System

Transvaginal ultrasound examination was performed on an empty urinary bladder using a sector transducer (5-8 MHz) with a 210°/240° image section (Acuson Sequoia Echo Ultrasound System, Calif., USA). Ultrasound information from these patients were recorded using a simple scoring system to evaluate the malignant status of ovarian tumors based on 1) presence of cystic or solid tumor, 2) presence of solid area in cyst, 3) presence of septa and 4) blood flow described earlier (Daskalakis at al., 2004). These morphological criteria permit us to overcome subjective interpretation of ovarian lesions and to assess a precise role for this diagnostic technique in the work-up of patients with persistent ovarian lesions. An overall score greater than three was regarded as cut-off value in differentiating malignant from benign ovarian tumors. Following surgery a comparison of the ultrasonographic and histopathological findings was made.

Statistical Analysis

For comparison of the differences between mean of haptoglobin concentration in cyst fluid of benign and malignant ovarian cancer, independent sample t-test was carried out using the SPSS 11.0 software. The Pearson's correlation analysis was performed to evaluate any relationship in the concentrations of haptoglobin measured by PHASE RANGE method and ELISA procedures. Receiver operating characteristic (ROC) curves were performed to assess the performance of biomarkers in cyst fluid using split-point analysis based on previous study. Fifty-five thresholds for each biomarker were set to minimize false positive and false negative ratios.

Results

Mass Spectrometry Analysis

One-dimensional gel electrophoresis, MALDI-TOF-MS-MS analysis and immunocapture experiments confirmed haptoglobin-α2 subunit as a potential biomarker for malignant ovarian tumours. SELDI-TOF analysis showed the presence of a potential biomarker of around 17 kDa.

FIG. 1 shows representative SELDI profiles ranging from 7 kDa-20 kDa according to the m/z ratio. The protein profiles of cyst fluid from epithelial ovarian cancer showed the presence of a high intensity peak with the mean of intensity of 3.23±0.85 at 17 kDa which was greatly diminished or absent in the benign tumours.

Figure 2:
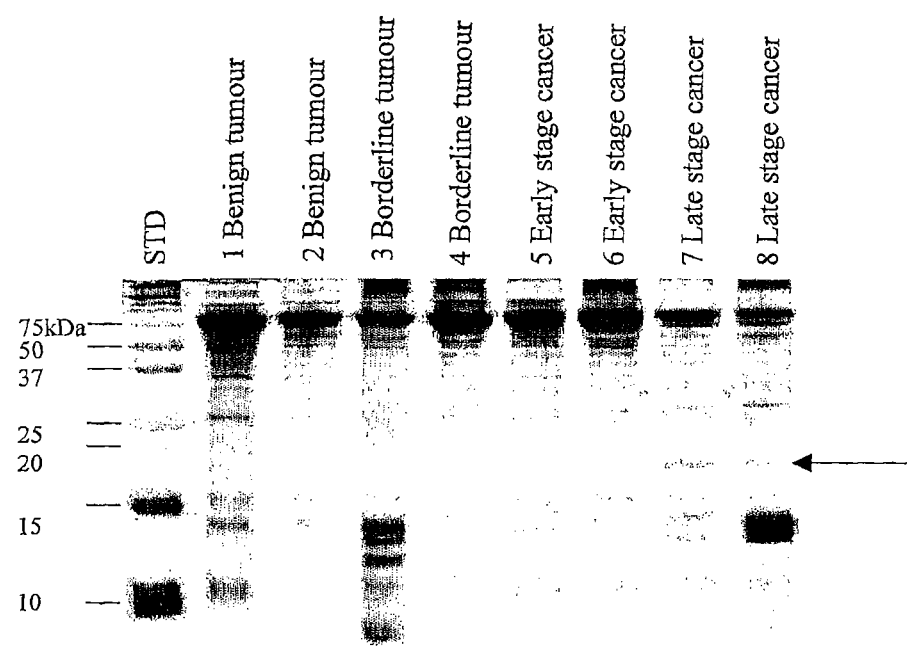
FIG. 2. One-dimensional gel electrophoresis of representative cyst fluid protein samples from ovarian tumours. The protein band indicated between 15-20 kDa was the corresponding unique protein with a molecular weight of 17 kDa peak which was also subjected to SELDI analysis. Lanes 1 and 2 represent benign ovarian tumours; lanes 3 and 4 represent borderline tumours; lanes 5 and 6 represent early stage ovarian cancer; and lanes 7 and 8 represent late stage ovarian cancer.

FIG. 2 indicates the protein bands between 15 kDa to 20 kDa which were predominantly expressed in cyst fluids of ovarian cancer samples compared to cyst fluids of benign ovarian tumours. The selected protein bands were excised from the gel and subjected to in-gel digestion followed by tandem MALDI-TOF-MS/MS analysis. Corresponding spectra of the protein was used for protein search in the NCBI database by peptide mass fingerprinting. Four most intense peptides were selected for MS/MS analysis. The matched peptides of the sequence have a 74% homology to that of haptoglobin-α2 subunit.

Mass spectrometry of proteins from biological fluids resolved by gel electrophoresis typically requires protein in the microgram range (Mortz et al, 1994). The cyst fluid from patients presenting with early and late stage epithelial ovarian carcinomas are endowed with abundant proteins and are therefore appropriate for this evaluation. In order to find out the identity of the potential protein marker with the mass of around 17 kDa, which distinguished ovarian cancer from benign tumours; we utilized SDS-PAGE to separate the protein mixtures and isolate the corresponding protein bands between 15-20 kDa.

Figure 3:
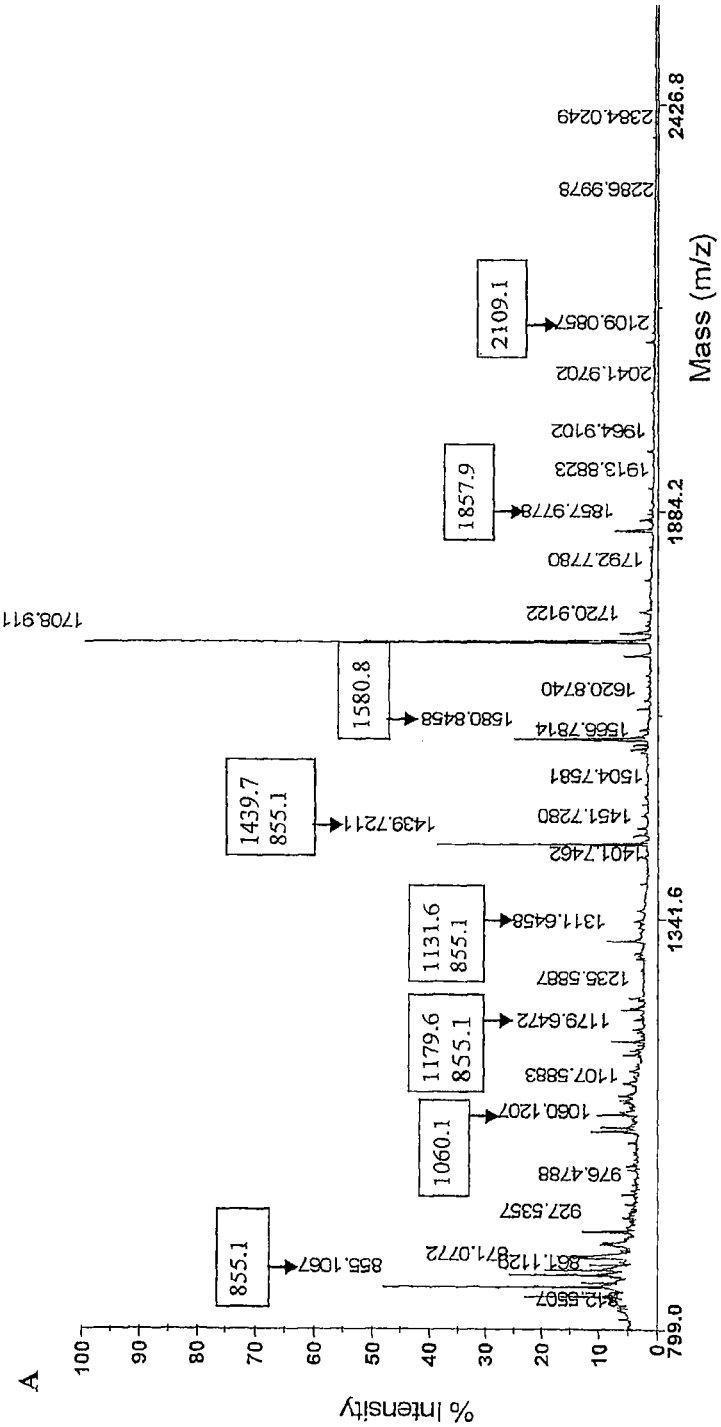
FIG. 3. Mass spectrum generated by the 15~20 kDa protein using MALDI-TOF/MS. Arrows at the mass spectrum peaks represent peptides from haptoglobin-$\alpha 2$ subunits.
Figure 5:
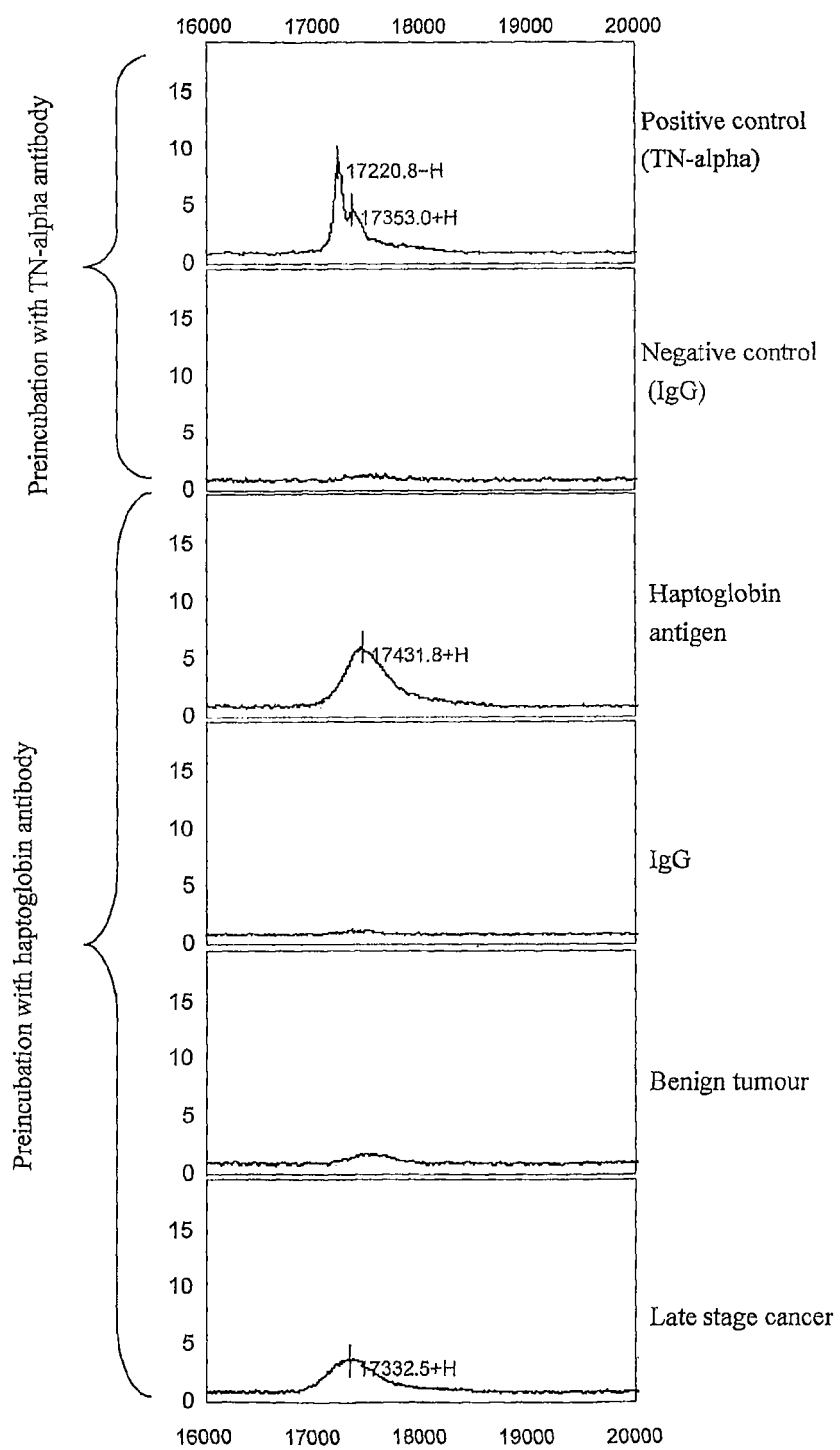
FIG. 5. Immunocapture experiments were done with the PS20 protein chip preincubated with anti-haptoglobin. 5 mg/ml haptoglobin (Graph 1) antigen was preincubated with DTT (room temperature for 1 hour) as the positive control and Bovine IgG as the negative control (Graph 2). Cyst fluid protein from late stage ovarian cancer and benign tumor were exposed to the antibody-coated arrays.

The explicit protein profiles using this high throughput analysis confirmed presence of haptoglobin α2-subunit (FIG. 3). A summary of the sequence information is shown below for SEQ ID NO:4 while the peptide sequences ascertained by MS/MS analysis are depicted in Table 1. To reconfirm that haptoglobin in SDS-PAGE is the corresponding peak from the proteinChip and immunocapture experiments, the proteinChip experiment was repeated with the difference that PS20 proteinChip was preincubated with anti-haptoglobin. Results from this procedure provided confirmatory evidence that the 17 kDa peak is haptoglobin identified in the SDS-PAGE (FIG. 5).

SEQ ID NO:4 is the sequence of human haptoglobin-α2 subunit (NCBI database accession No. 701184A) and the matched peptide sequence is bold and underlined. Sequence coverage is 74%

```
                                              (SEQ ID NO: 4)
VNDSGNDVTD IADDGQPPPK CIAHGYVEHS VRYQCKNYYK

LRTQGDGVYT LNNEKQWINK AVGDKLPECE ADDGQPPPKC

IAHGYVEHSV RYQCKNYYKL RTQGDGVYTL NNEKQWINKA

VGDKLPECEA VGKPKNPANP VQ
```

TABLE 1

The peptide sequence from four most intense peaks observed in the mass spectra using MS/MS analysis.

| Mr Observed | (expt) | Start | End | Ions | Peptide (SEQ ID NO) |
|---|---|---|---|---|---|
| 1439.72 | 1438.71 | 60 | 72 | 106 | TEGDGVYTLNDKK (5) |
| 1580.85 | 1579.84 | 58 | 71 | 17 | LRTEGDGVYTLNDK (6) |
| 1708.91 | 1707.90 | 117 | 131 | 49 | LRTEGDGVYTLNNEK (7) |

TABLE 1-continued

The peptide sequence from four most intense peaks observed in the mass spectra using MS/MS analysis.

| Mr Observed | (expt) | Start | End | Ions | Peptide (SEQ ID NO) |
|---|---|---|---|---|---|
| 1857.98 | 1856.97 | 137 | 153 | 29 | AVGDKLPECEAVCGKPK (8) |

Western Blotting Analysis

Figure 4:
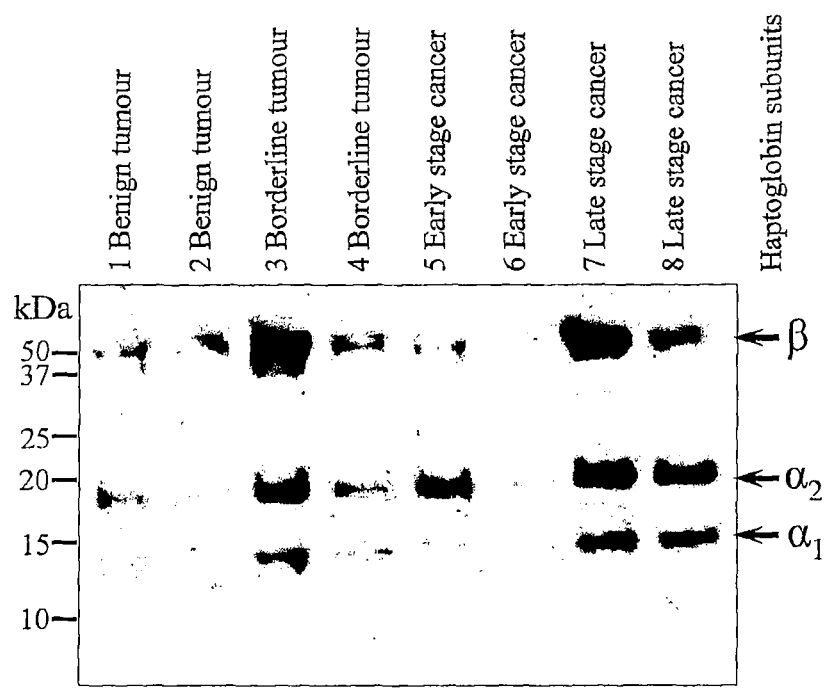
FIG. 4. Confirmation of presence of haptoglobin subunits in cyst fluid from ovarian tumour by Western blotting. Equal amounts of protein (10 ug) from benign ovarian tumour (Lane 1 and 2); borderline ovarian tumour (Lane 3 and 4); early stage ovarian cancer (Lane 5 and 6) and late stage ovarian cancer (Lane 7 and 8) were loaded on the 15% SDS-PAGE. Elevation of haptoglobin in cyst fluid of cancer (lane 7-8) could be detected by western blotting compared with benign cases (lane 1-2).

To further confirm the identity of the protein, we performed western blotting analysis using polyclonal rabbit anti-human haptoglobin antibody to detect the different subunits of haptoglobin. Results from the blotting procedure indicated the presence of different subunits of haptoglobin in cyst fluid from epithelial ovarian tumours (FIG. 4). Based on molecular weight, the corresponding subunits identified were β (40 kDa); α2 (16.5 kDa) and α1 (9 kDa).

These results, together with the SELDI and SDS-PAGE data, clearly indicated that haptoglobin levels were elevated in epithelial ovarian cancer when compared with benign disease.

Having now generally described the invention, the same will be more readily understood through reference to the following examples that are provided by way of illustration and are not intended to be limiting of the present invention.

EXAMPLES

Example 1

Quantitative Validation by Enzyme-Linked Immunosorbent Assay

Figure 6:
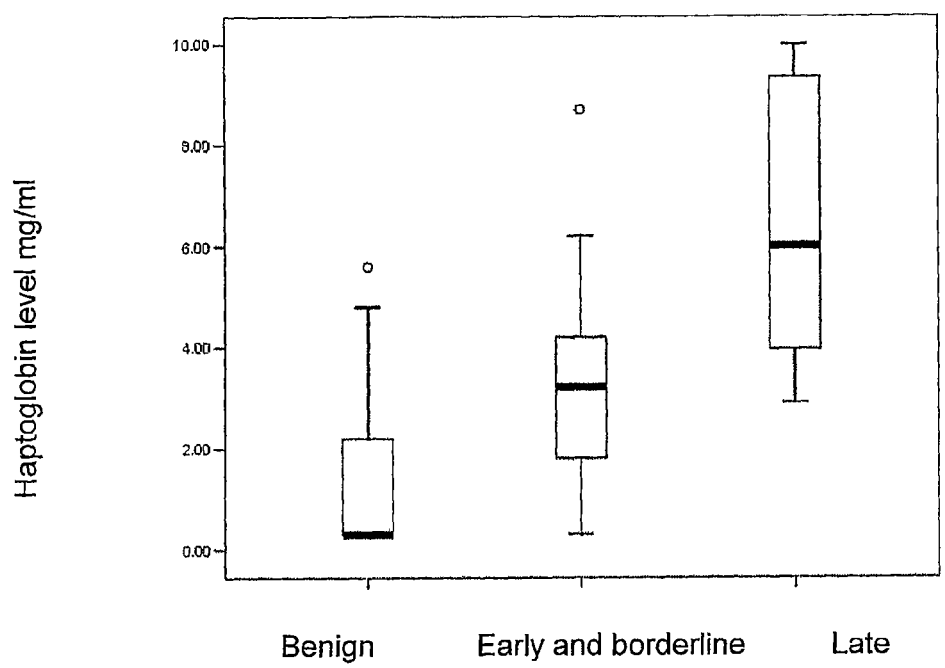
FIG. 6. Box plot of haptoglobin (A) or haptoglobin α-subunit (B) levels in benign ovarian tumor; early and late stage ovarian cancer as determined by a sandwich ELISA method as described in Example 5.
Figure 6:
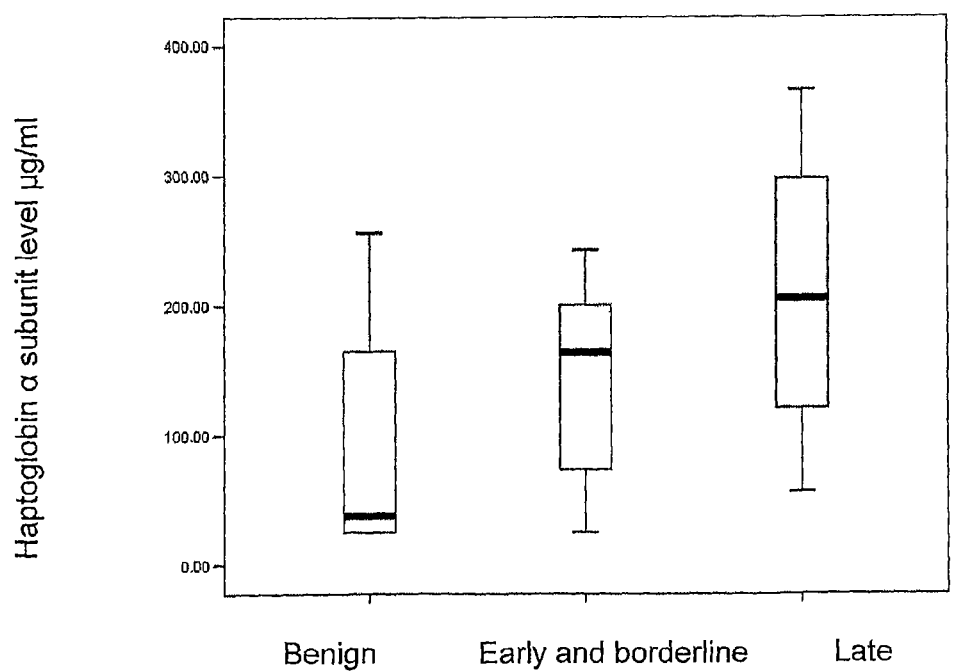

To further explore and quantify the total cyst fluid haptoglobin or Hp α-subunit levels, an in-house sandwich ELISA method was established. Three samples of different concentrations were tested 8 times on the same day (intra-assay) and repeated on 5 consecutive days (inter-assay). The coefficients of variance (CV) were 3.8% and 14.2% for the intra-assay and inter-assays for Hp; 4.5% and 13.2% for Hp α-subunit assay, respectively. Comparison of the mean of Hp or Hp α-subunit levels in benign subjects and those presenting with early and late stage cancer were analyzed using ANOVA analysis. A significant difference between the three groups of patients was observed as indicated in Table 2 and a prognosis based on the disease stage identified can thus be obtained. A boxplot of the data is given in FIG. 6.

TABLE 2

| Group | No. | Hp level (mg/ml) Mean | P | Hp α-subunit (ug/ml) Mean | P |
|---|---|---|---|---|---|
| Late Cancer | 15 | 6.35 | <0.001 | 216.3 | <0.001 |
| Early Cancer | 11 | 3.33 | <0.05 | 137.9 | |
| Benign | 35 | 1.43 | | 71.4 | |

Thus it is possible to diagnose and grade the cancer by measuring the level of haptoglobin protein, fragment or derivative thereof, in cyst fluid using the ELISA technique.

Example 2

Quantitative Validation by the Phase Range Haptoglobin Assay Kits

The difference in OD value at 3 minute and 5 minute time points for the PHASE RANGE assays in cyst fluid from benign and malignant ovarian tumours were analyzed using the SPSS 13.0 software. A significant difference in the intensity of colour development was observed in 25 out of 28 samples (89%) from epithelial ovarian cancer patients when compared with those presenting with benign tumours (FIG. 7).

Figure 7:
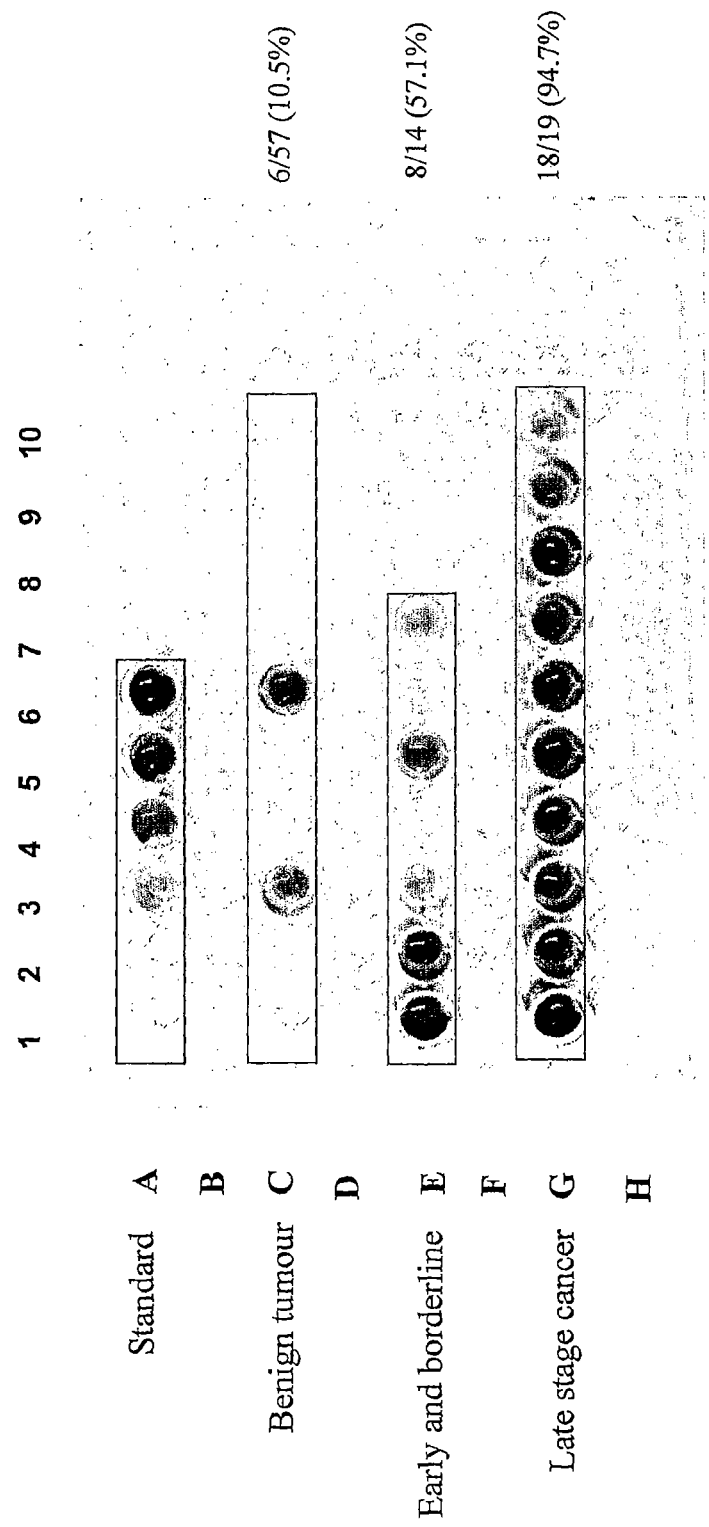
FIG. 7. Representative results obtained from the PHASE RANGE Haptoglobin assay for benign (Lane C), early (Lane E) and late stage (Lane G) cancer. Lane A demonstrates the color change in controls of varying haptoglobin concentrations. In benign cases, in 6 out of 57 samples (10.5%), the test was positive i.e. there was a color change in the assay. In early cases, in 8 out of 14 samples (57.1%), the test was positive i.e. there was a color change in the assay. In malignant cases, in 18 out of 19 samples (94.7%), the test was positive i.e. there was a color change in the assay.
Figure 8:
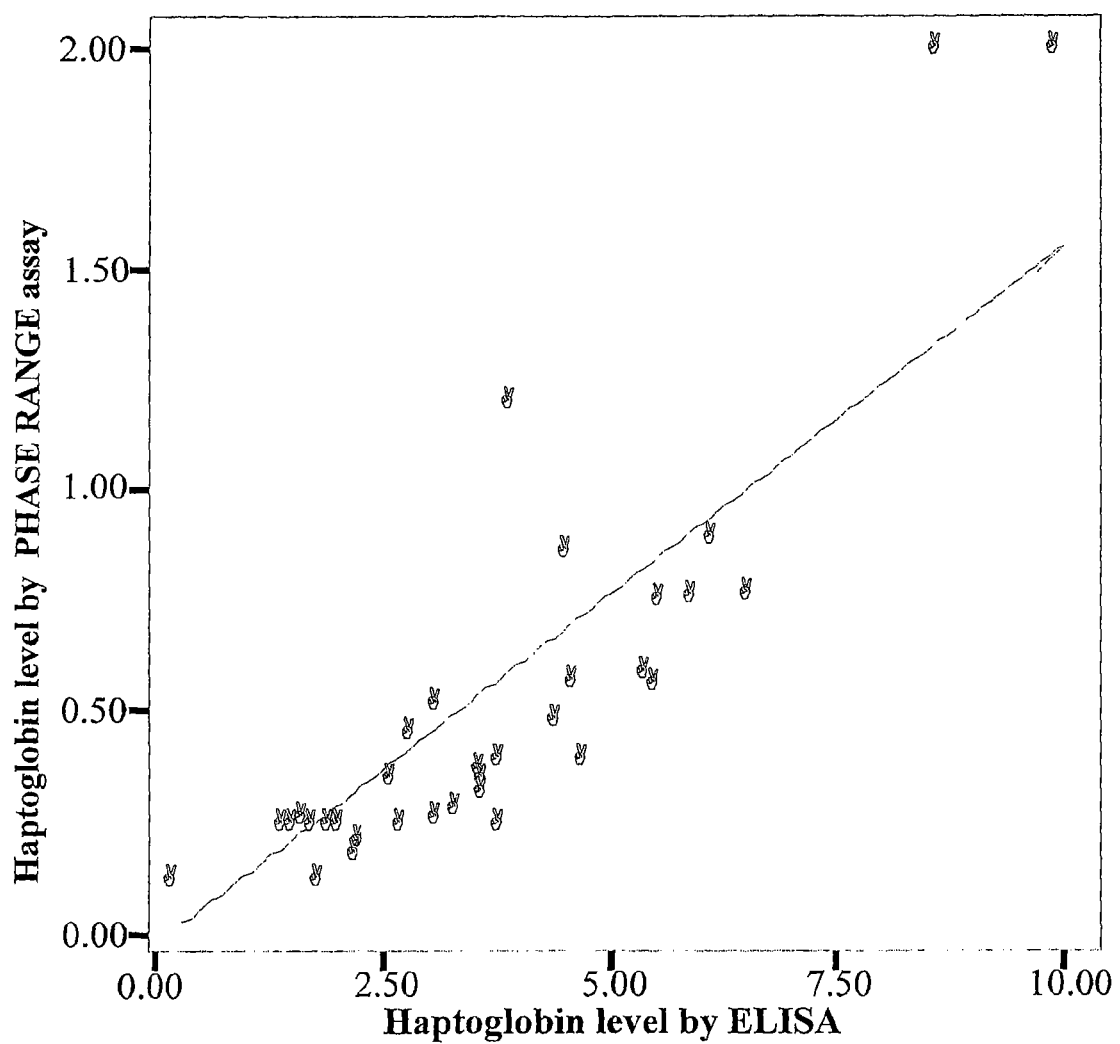
FIG. 8. Pearson's correlation between haptoglobin levels measured by ELISA and the PHASE RANGE assays (positive correlation, $r^2$=0.79). Haptoglobin level (PHASE)=−0.02+0.16*Haptoglobin level (ELISA).

Moreover, as indicated in FIG. 7, there was a significant positive correlation between the levels of haptoglobin measured by ELISA and the PHASE RANGE assays with a Pearson's correlation coefficient r square value of 0.81. Measurements of cyst fluid haptoglobin by either method would therefore be useful in the differentiation of benign from malignant ovarian cancers, and also for the prognostic evaluation of the cancer. Based on these criteria, our data indicates that the 5-minute PHASE RANGE assays of haptoglobin would be a rapid and useful predictor of malignancy in patients presenting with this insidious disease. This rapid assay dye-binding method is useful on its own or as an adjunct to other diagnostic measures such as frozen section techniques currently employed in established oncology centres and will enable the gynaecologist to discern malignant status during the operative procedure.

Example 3

Haptoglobin Measurement in Conjunction with Other Diagnostic Measures

Ultrasound Evaluation

Using transvaginal color Doppler ultrasound we correctly identified 25 out of 28 malignant tumors as well as 24 out of 33 benign tumours. Sensitivity and specificity of the color Doppler ultrasound were 89.3% and 72.7% respectively. The positive and negative predictive values (PPV and NPV respectively) of the method were 52.2% and 88.4% respectively.

Figure 9:
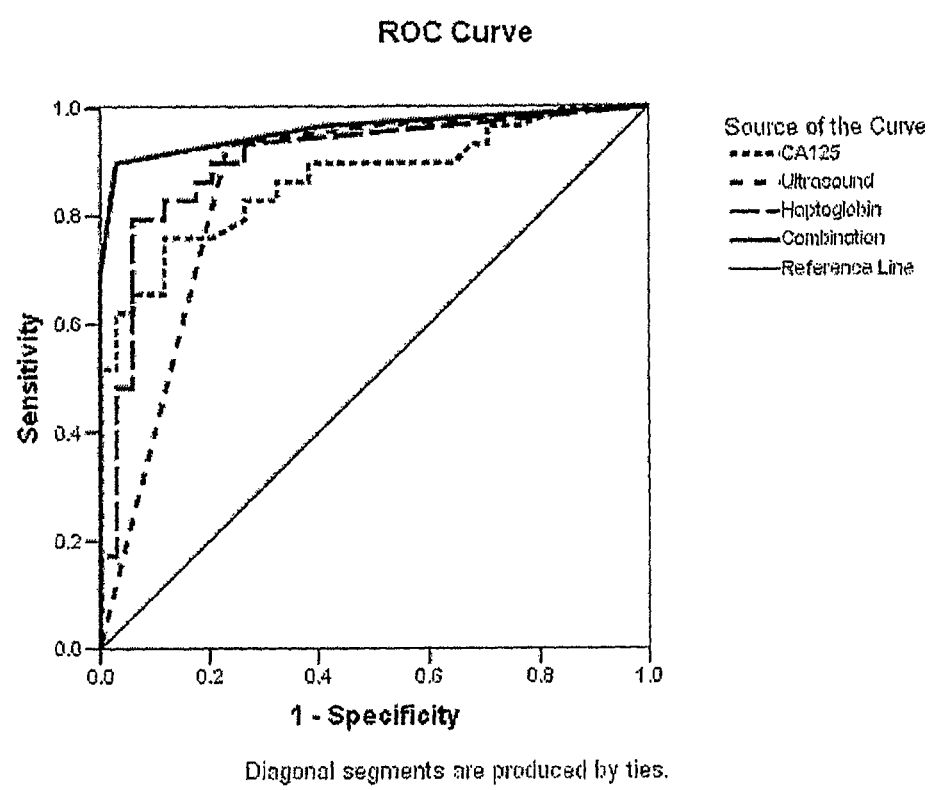
FIG. 9. Receiver operating characteristic (ROC) curves for Haptoglobin, CA125 and ultrasound analysis, and a combination of the three using split point analysis.

Multivariate analysis of haptoglobin in combination with CA-125 and ultrasound The haptoglobin dye binding assay alone was observed to possess 89% sensitivity; 91% specificity; 76.7% positive predictive value (PPV) and 96.8% negative predictive value (NPV) respectively. ROC (receiver operating characteristic) curves for haptoglobin in cyst fluid, CA-125 levels in serum and ultrasonography were then conducted to examine the ability of these parameters to better differentiate malignant from benign ovarian tumors. It showed that haptoglobin had an enhanced predictive performance when combined with CA-125 and ultrasound parameters giving an area under curve (AUC) of 0.957 with a 95% confidence interval of 0.903-1.012 (FIG. 9). Moreover, a combination of the three parameters in our patients was observed to have 89% sensitivity and 94.3% specificity with a PPV of 83.9% and NPV of 96.4% for ovarian cancers (Table 3).

TABLE 3

|  | AUC | 95% C.I. |
| --- | --- | --- |
| Combination | 0.957 | 0.903-1.012 |
| Ultrasound | 0.853 | 0.753-0.952 |
| CA-125 | 0.866 | 0.773-0.952 |
| Hp | 0.903 | 0.821-0.984 |

Thus, use of a combination of multivariate measures with the quantitation of haptoglobin from cyst fluid provide for sensitive detection of ovarian cancer with high confidence.

Kit

Example 4

Diagnostic and Prognostic Kit

The present invention also provides a diagnostic and/or prognostic kit comprising at least one molecule or compound reactive to the haptoglobin protein. The reaction may be that of a binding or hybridization reaction such as that of an anti-haptoglobin antibody recognising and binding to a haptoglobin protein, derivative, mutation or fragment thereof. The reaction may also be that of a chemical or enzymatic reaction wherein the peroxidising activity of a hemoglobin-haptoglobin complex reacts with a substrate molecule and the reaction is detected colorimetrically Use of the Invention Ovarian cancer progression is associated with the accumulation of cyst fluid in the ovarian cyst within the abdominal cavity, Haptoglobin is a genetically determined α2-acidic glycoprotein with haemoglobin-binding capacity (Bowman et al., 1982), present in most body fluids of humans and other mammals. It is predominantly synthesized by the liver and it functions as an antioxidant and, by virtue of binding to haemoglobin, prevents oxidative tissue damage that may be mediated by free haemoglobin, Langlois et al. (1996).

Data from our study have shown that haptoglobin serves as a marker in cyst fluid of patients presenting with epithelial ovarian cancer. We used SELDI analysis and SDS-PAGE procedures to detect the presence of a 17 kDa protein which was predominantly present in cyst fluid from cancer patients with malignant tumours as compared to those with benign tumours. This protein was later identified as haptoglobin using the MALDI-TOF-MS/MS approach. Identity of this glycoprotein was further confirmed using western blotting analysis. Moreover, a sandwich ELISA method also indicated a significant difference in the concentration of this biomarker between the cancer and benign groups examined (P<0.001). The overall diagnostic accuracy using haptoglobin and CA-125 levels with ultrasound parameters were as follows: sensitivity 89%, specificity 94.3%, positive predictive value (PPV) 83.9% and negative predictive value (NPV) 96.4% respectively. However, using the haptoglobin dye binding assay alone it was observed to possess 89% sensitivity; 91% specificity; 76.7% PPV and 96.8% NPV respectively. Our data demonstrates haptoglobin to be a reliable biomarker which could enable the rapid detection of malignancy.

A comparison of the SELDI-TOF, SDS-PAGE protein profiles and western blotting confirmed a 17 kDa peptide identified as haptoglobin-α2 subunit. Similarly our in-house ELISA technique for the haptoglobin molecule indicated significantly higher concentrations of this glycoprotein in cyst fluid from early and late stage epithelial ovarian cancer compared to those presenting with benign diseases.

Elevation of haptoglobin in sera and ascites of ovarian cancer has been reported in previous studies using the ELISA method (Elg et al., 1993). Recently, proteomics-based approaches have been utilized to discover and identify novel proteins as potential diagnostic biomarkers. Ye et al. (2003) have identified haptoglobin α-subunit as potential serum biomarker in ovarian cancer with a sensitivity of 95% and a specificity of 91% combined with CA-125. However, there was no teaching or suggestion that haptoglobin from cyst fluid may be used as a biomarker for ovarian cancer.

Using the SELDI-TOF analysis, we found that a peak at approximately 17 kDa was predominantly found in late stage ovarian cancers. SDS-PAGE and MALDI-TOF-MS/MS were used to identify this particular protein as haptoglobin-α subunit. Moreover, using the in-house sandwich ELISA method, we have demonstrated that haptoglobin concentrations were significantly elevated in cyst fluid of epithelial ovarian cancer when compared with benign tumours. From the present invention, a simple cut-off measurement can be used as a reliable predictor of malignancy.

This has important clinical implications since in our experience, the PHASE RANGE haptoglobin assay is a reliable method of confirming malignancy in ovarian cancer. Determination of ovarian cancer is currently conducted by frozen section of ovarian tissue by a pathologist during surgery. In our experience, the use of the PHASE RANGE kit at a cut-off time of 5 min enabled the differentiation of malignant from benign epithelial ovarian tumours with the general characteristics of the test having 89% sensitivity; 91% specificity; 76.7% PPV and 96.8% NPV respectively. In comparison, the frozen section technique is both expensive and time consuming and in many medical institutions or clinical establishments, it is dependent on the availability of an attending pathologist. The method of the present invention can involve a combination of the three parameters, haptoglobin, CA125 and ultrasonography in our patients to obtain enhanced diagnostic accuracy compared with the use of any single parameter.

Nevertheless, when considered by itself, haptoglobin is a viable diagnostic marker capable of detecting malignancy of these tumours with an AUC of 0.903 (FIG. 9; Table 3).

Previous studies, however, have indicated that general population screening of serum protein markers with a minimum PPV of 10% (i.e. no more than nine false positives for each true positive) will be of benefit in epithelial ovarian cancer discrimination. This is however not feasible and cost-effective in a clinical setting in which there occurs a low prevalence of this cancer in women, as it has been calculated that a 99.6 percent of specificity is required for any ovarian cancer screening test to have a true impact (Mor et al., 2005). In this study, however, we selected only those patients with ovarian cyst in order to differentiate malignant from benign ovarian cyst during the operative procedure. This measure would enhance the relatively high prevalence of ovarian cancer in our study group, the PPV of which was observed to be 83.9%. Based on this criterion, we highlight a simple time point cut-off for the haptoglobin color reaction in cyst fluid which could be effectively utilized in the operation theatre for identifying malignancy which greater ease and rapidity.

The reports of Bin Ye et al and Ahmed et al have focused on the proteomic identification of haptoglobin precursors or subunits in the sera of women with ovarian cancer and their possible role as tumour markers (Ye et al., 2003; Ahmed et al., 2004). However, the main source of circulating haptoglobin in humans is the liver and the rise of serum haptoglobin contributed by malignant disease has not been well studied. It is also a non-specific marker which is elevated in various other conditions, hence its validation as a clinically useful serum tumour marker may be difficult to ascertain.

However, using immunohistochemical techniques Ahmed et al. (2004) has also reported absence of haptoglobin activity in normal ovarian tissue but moderate to strong staining was observed in tissues from ovarian cancer. The identification of significantly increased levels of haptoglobin in ovarian cancer cyst fluid identified by us may have more important clinical implications.

Intra-operative cyst fluid determination of haptoglobin levels using a simple test kit with a specific cut-off value allows identification of women who may require further pathological assessment with frozen section and hence, a more complex operative procedure could be instituted. It has been documented that initial surgery performed by a trained gynecological oncologist has a favorable impact on long term survival of patients with this disease (Guidelines, Gynecol Oncol, 2000). Such a procedure will allow the proper surgical staging of ovarian cancers and thus obviates the need for repeat surgery in malignancies which have been misdiagnosed as "benign" cysts. The haptoglobin biomarker possesses the potential to reflect the malignant status of the afflicted women and would positively impact on the clinical outcome.

Even a negative result for the method of present invention is informative. As more ovarian cysts are being operated on laproscopically, a negative result will indicate that the cyst is not cancerous and the surgeon can proceed with the cystectomy with a higher level of confidence.

It will be apparent to a person skilled in the art that the present invention may also be used in veterinary medicine for animals. While specific examples to practice the invention have been provided, it will be appreciated that various modifications and improvements may be made by a person skilled in the art without departing from the spirit and scope of the present invention.

REFERENCES

Ahmed N, Barker G, Oliva K T, et al. Proteomic-based identification of haptoglobin-1 precursor as a novel circulating biomarker of ovarian cancer. Br J Cancer; 91(1):129-40 (2004)

Boss E A, Massuger L F, Thomas C M, et al. Clinical value of components of the plasminogen activation system in ovarian cyst fluid. Anticancer Res; 22(1A):275-82 (2002)

Bowman B H, Kurosky A. Haptoglobin: the evolutionary product of duplication, unequal crossing over, and point mutation. Adv Hum Genet; 12:189-261, 453-4 (1982)

Bradford M M Anal. Biochem. 72, 248 (1976)

Canis et al. Frozen section in laparoscopic management of macroscopically suspicious ovarian masses. J Am Assoc Gynecol Laparosc; 11:365-9 (2004).

Cannistra S A. Cancer of the ovary. N Engl J. Med. 1993; 329(21): 1550-1559

Darai E, Detchev R, Hugol D, Quang N T. Serum and cyst fluid levels of interleukin (IL)-6, IL-8 and tumour necrosis factor-alpha in women with endometriomas and benign and malignant cystic ovarian tumours. Hum Reprod; 18(8): 1681-5 (2003)

Daskalakis G, Kalmantis K, Skartados N, Thomakos N, Hatziioannou L, Antsaklis A. Assessment of ovarian tumors using transvaginal color Doppler ultrasonography. Eur J Gynaecol Oncol; 25(5):594-6 (2004).

Devarbhavi H, Kaese D, Williams A W, Rakela J, Klee G G, Kamath P S. Cancer antigen 125 in patients with chronic liver disease. Mayo Clin Proc; 77(6):538-41 (2002)

Elg S A, Carson L F, Fowler J M, Twiggs L B, Moradi M M, Ramakrishnan S. Ascites levels of haptoglobin in patients with ovarian cancer. Cancer; 71(12):3938-41 (1993)

Guidelines for referral to a gynecologic oncologist: rationale and benefits. The Society of Gynecologic Oncologists. Gynecol Oncol; 78(3 Pt 2):S1-13 (2000).

Jacobs I J, Menon U. Progress and challenges in screening for early detection of ovarian cancer. Mol Cell Proteomics; 3(4):355-66 (2004)

Jacobs I J, Skates S J, MacDonald N, et al. Screening for ovarian cancer: a pilot randomised controlled trial. Lancet; 353(9160):1207-10 (1999)

Jennings T S, Dottino P R. The application of operative laparoscopy to gynecologic oncology. Curr Opin Obstet. Gynecol.; 6(1):80-5 (1994).

Karlan B Y, Baldwin R L, Lopez-Luevanos E, et al. Peritoneal serous papillary carcinoma, a phenotypic variant of familial ovarian cancer: implications for ovarian cancer screening. Am J Obstet Gynecol; 180(4):917-28 (1999)

Kristensen G B., Trope C. Epithelial ovarian carcinoma. Lancet. 1997; 349(9045): 113-117.

Langlois M R, Delanghe J R. Biological and clinical significance of haptoglobin polymorphism in humans. Clin Chem; 42(10):1589-600 (1996)

Lim et al., 1997 Lim F K, Yeoh C L, Chong S M, Arulkumaran S. Pre and intraoperative diagnosis of ovarian tumours: how accurate are we? Aust N Z J Obstet. Gynaecol. 1997 May; 37(2):223-7

Mackey S E, Creasman W T. Ovarian cancer screening. J Clin Oncol; 13(3):783-93 (1995)

Maiman M, Seltzer V, Boyce J Laparoscopic excision of ovarian neoplasms subsequently found to be malignant. Obstet. Gynecol.; 77(4):563-5 (1991).

Michel G, De Iaco P, Castaigne D et al. Extensive cytoreductive surgery in advanced ovarian carcinoma. Eur J Gynaec Oncol; 18: 9-15 (1997).

Mor G, Visintin I, Lai Y, et al. Serum protein markers for early detection of ovarian cancer. Proc Natl Acad Sci USA; 102(21):7677-82 (2005)

Mortz E, Vorm O, Mann M, Roepstorff P. Identification of proteins in polyacrylamide gels by mass spectrometric peptide mapping combined with database search. Blot Mass Spectrom; 23(5):249-61 (1994)

Robinson W R, Curtin J P, Morrow C P. Operative staging and conservative surgery in management of low malignant potential ovarian tumors. Int J Gynecol Cancer; 2:113-8 (1992).

Vergote I B, De Waver I, Decloedt J et al. Neoadjuvant chemotherapy or primary debulking surgery in advanced ovarian carcinoma: a retrospective analysis of 285 patients. Gynecol Oncol; 71: 431-436 (1998).

Wingo, P. A., Ries, L. A., Rosenberg, H. M., Miller D. S., Edwards B. K. Cancer incidence and mortality, 1973-1995: a report card for the U.S.: Cancer 1998; 82: 1197-1207.

Woolas R P, Oram D H, Jeyarajah A R, Bast R C, Jacobs I J. Ovarian cancer identified through screening with serum markers but not by pelvic imaging. Int J Gynecol Cancer; 9(6):497-501 (1999)

Ye B, Cramer D W, Skates S J, et al. Haptoglobin-alpha subunit as potential serum biomarker in ovarian cancer: identification and characterization using proteomic profiling and mass spectrometry. Clin Cancer Res; 9(8):2904-11 (2003)

Yeo E L K, Ju K M, Poddar N C, Hui P K, Tang L C H. The accuracy of intraoperative frozen section in the diagnosis of ovarian tumors. J Obstet Gynaecol; 24:189-95 (1998).

Zhang R, Barker L, Pinchev D, et al. Mining biomarkers in human sera using proteomic tools. Proteomics; 4(1):244-56 (2004)

U.S. Pat. No. 6,451,550

The invention claimed is:

1. A method of diagnosing and/or detecting the presence of ovarian cancer in a subject, the method comprising:
   (a) providing at least one cyst fluid sample from a subject;
   (b) determining the expression of haptoglobin protein in the cyst fluid sample;
   (c) comparing the expression of the haptoglobin protein in the cyst fluid sample with that of a benign ovarian cyst, and
   (d) treating said subject for ovarian cancer;
   wherein step (d) is only performed if said expression of said haptoglobin protein in said cyst fluid sample is significantly increased compared to the expression in said benign ovarian cyst.

2. The method according to claim 1, wherein the haptoglobin protein is human haptoglobin protein.

3. The method according to claim 1, wherein the sequence of the haptoglobin protein is given in SEQ ID NO:2.

4. The method according to claim 1, wherein the method further comprises at least one CA-125 measurement on the sample(s).

5. The method according to claim 1, wherein the method further comprises at least one ultrasound evaluation of the subject.

6. A method of monitoring the efficacy of a treatment for ovarian cancer in a subject, the method comprising:
   (a) providing at least two cyst fluid samples from the subject, wherein the at least two samples comprise a first sample obtained before treatment of the subject and a second sample obtained after treatment of the subject;
   (b) determining the expression of a haptoglobin protein; and
   (c) comparing the expression of the haptoglobin protein in the at least two samples,
   wherein a significant increase in expression in the first sample obtained before treatment indicates the efficacy of treatment for ovarian cancer in the subject.

7. The method according to claim 6, wherein the sequence of the haptoglobin protein is given in SEQ ID NO:2.

8. The method according to claim 6, wherein the method further comprises at least one CA-125 measurement on the sample(s).

9. The method according to claim 6, wherein the method further comprises at least one ultrasound evaluation of the subject.

10. The method according to claim 1 or 6, wherein the expression of haptoglobin protein is measured by determining the presence of:

(a) total haptoglobin protein; and/or
(b) at least one subunit of the haptoglobin protein.

11. The method according to claim 1 or 6, wherein the expression of haptoglobin protein is measured by determining the presence of α-subunit or β-subunit of the haptoglobin protein.

12. The method according to claim 11, wherein the α-subunit of the haptoglobin protein is the α2-subunit.

13. The method according to claim 1 or 6, wherein the expression of haptoglobin protein is determined using at least one antibody.

14. A method of diagnosing and/or detecting the presence of ovarian cancer in a subject, the method comprising:
    (a) providing at least one cyst fluid sample from a subject;
    (b) determining the expression of haptoglobin protein and CA-125 in the cyst fluid sample; and
    (c) comparing the expression of the haptoglobin protein in the cyst fluid sample with that of a benign ovarian cyst;
    wherein a significant increase in expression indicates the presence of ovarian cancer in the subject.

15. A method of diagnosing and/or detecting the presence of ovarian cancer in a subject, the method comprising:
    (a) providing at least one cyst fluid sample from a subject;
    (b) determining the expression of haptoglobin protein and CA-125 in the cyst fluid sample;
    (c) comparing the expression of the haptoglobin protein in the cyst fluid sample with that of a benign ovarian cyst; and
    (d) performing an ultrasound evaluation on the subject;
    wherein a significant increase in expression indicates the presence of ovarian cancer in the subject.

* * * * *

SEQUENCE LISTING

```
<160> NUMBER OF SEQ ID NOS: 8

<210> SEQ ID NO 1
<211> LENGTH: 1433
<212> TYPE: DNA
<213> ORGANISM: Homo sapiens

<400> SEQUENCE: 1
agatgcccca cagcactgct cttccagagg caagaccaac caagatgagt gccctgggag      60
ctgtcattgc cctcctgctc tggggacagc tttttgcagt ggactcaggc aatgatgtca     120
cggatatcgc agatgacggc tgcccgaagc cccccgagat tgcacatggc tatgtggagc     180
actcggttcg ctaccagtgt aagaactact acaaactgcg cacagaagga gatggagtat     240
acaccttaaa tgataagaag cagtggataa ataaggctgt tggagataaa cttcctgaat     300
gtgaagcaga tgacggctgc ccgaagcccc cgagattgc acatggctat gtggagcact     360
cggttcgcta ccagtgtaag aactactaca aactgcgcac agaaggagat ggagtgtaca     420
ccttaaacaa tgaagcag tggataaata aggctgttgg agataaactt cctgaatgtg     480
aagcagtatg tgggaagccc aagaatccgg caaacccagt gcagcggatc ctgggtggac     540
acctggatgc caaaggcagc tttccctggc aggctaagat ggtttcccac cataatctca     600
ccacaggtgc cacgctgatc aatgaacaat ggctgctgac cacggctaaa aatctcttcc     660
tgaaccattc agaaaatgca acagcgaaag acattgcccc tactttaaca ctctatgtgg     720
```

```
ggaaaaagca gcttgtagag attgagaagg ttgttctaca ccctaactac tcccaggtag    780
atattgggct catcaaactc aaacagaagg tgtctgttaa tgagagagtg atgcccatct    840
gcctaccttc aaaggattat gcagaagtag ggcgtgtggg ttatgttcct ggctgggggc    900
gaaatgccaa tttaaatttt actgaccatc tgaagtatgt catgctgcct gtggctgacc    960
aagaccaatg cataaggcat tatgaaggca gcacagtccc cgaaaagaag acaccgaaga   1020
gccctgtagg ggtgcagccc atactgaatg aacacacctt ctgtgctggc atgtctaagt   1080
accaagaaga cacctgctat ggcgatgcgg gcagtgcctt tgccgttcac gacctggagg   1140
aggacacctg gtatgcgact gggatcttaa gctttgataa gagctgtgct gtggctgagt   1200
atggtgtgta tgtgaaggtg acttccatcc aggactgggt tcagaagacc atagctgaga   1260
actaatgcaa ggctggccgg aagcccttgc ctgaaagcaa gatttcagcc tggaagaggg   1320
caaagtggac gggagtggac aggagtggat gcgataagat gtggtttgaa gctgatgggt   1380
gccagccctg cattgctgag tcaatcaata aagagctttc ttttgaccca ttt          1433

<210> SEQ ID NO 2
<211> LENGTH: 406
<212> TYPE: PRT
<213> ORGANISM: Homo sapiens

<400> SEQUENCE: 2

Met Ser Ala Leu Gly Ala Val Ile Ala Leu Leu Trp Gly Gln Leu
1               5                   10                  15

Phe Ala Val Asp Ser Gly Asn Asp Val Thr Asp Ile Ala Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Tyr Leu Asn Asp Lys Lys Gln Trp Ile Asp Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asp Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Leu Gln Lys Val
                245                 250                 255
```

-continued

```
Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala Asn
        275                 280                 285

Phe Lys Phe Thr Asp His Leu Lys Tyr Val Met Leu Pro Val Ala Asp
        290                 295                 300

Gln Asp Gln Cys Ile Arg His Tyr Glu Gly Ser Thr Val Pro Glu Lys
305                 310                 315                 320

Lys Thr Pro Lys Ser Pro Val Gly Val Gln Pro Ile Leu Asn Glu His
                325                 330                 335

Thr Phe Cys Ala Gly Met Ser Lys Tyr Gln Glu Asp Thr Cys Tyr Gly
            340                 345                 350

Asp Ala Gly Ser Ala Phe Ala Val His Asp Leu Glu Glu Asp Thr Trp
        355                 360                 365

Tyr Ala Thr Gly Ile Leu Ser Phe Asp Lys Ser Cys Ala Val Ala Glu
        370                 375                 380

Tyr Gly Val Tyr Val Lys Val Thr Ser Ile Gln Asp Trp Val Gln Lys
385                 390                 395                 400

Thr Ile Ala Glu Asn
            405

<210> SEQ ID NO 3
<211> LENGTH: 15
<212> TYPE: PRT
<213> ORGANISM: Artificial sequence
<220> FEATURE:
<223> OTHER INFORMATION: Sequence to generate polyclonal rabbit antibody
      against Hp alpha-subunit

<400> SEQUENCE: 3

Cys Lys Asn Tyr Tyr Lys Leu Arg Thr Gln Gly Asp Gly Val Tyr
1               5                   10                  15

<210> SEQ ID NO 4
<211> LENGTH: 142
<212> TYPE: PRT
<213> ORGANISM: Artificial sequence
<220> FEATURE:
<223> OTHER INFORMATION: Sequence to generate polyclonal rabbit antibody
      against Hp alpha-subunit

<400> SEQUENCE: 4

Val Asn Asp Ser Gly Asn Asp Val Thr Asp Ile Ala Asp Asp Gly Gln
1               5                   10                  15

Pro Pro Pro Lys Cys Ile Ala His Gly Tyr Val Glu His Ser Val Arg
            20                  25                  30

Tyr Gln Cys Lys Asn Tyr Tyr Lys Leu Arg Thr Gln Gly Asp Gly Val
        35                  40                  45

Tyr Thr Leu Asn Asn Glu Lys Gln Trp Ile Asn Lys Ala Val Gly Asp
    50                  55                  60

Lys Leu Pro Glu Cys Glu Ala Asp Asp Gly Gln Pro Pro Pro Lys Cys
65              70                  75                  80

Ile Ala His Gly Tyr Val Glu His Ser Val Arg Tyr Gln Cys Lys Asn
            85                  90                  95

Tyr Tyr Lys Leu Arg Thr Gln Gly Asp Gly Val Tyr Thr Leu Asn Asn
        100                 105                 110

Glu Lys Gln Trp Ile Asn Lys Ala Val Gly Asp Lys Leu Pro Glu Cys
        115                 120                 125
```

```
Glu Ala Val Gly Lys Pro Lys Asn Pro Ala Asn Pro Val Gln
    130                 135                 140
```

```
<210> SEQ ID NO 5
<211> LENGTH: 13
<212> TYPE: PRT
<213> ORGANISM: Homo Sapiens

<400> SEQUENCE: 5

Thr Glu Gly Asp Gly Val Tyr Thr Leu Asn Asp Lys Lys
1               5                   10

<210> SEQ ID NO 6
<211> LENGTH: 14
<212> TYPE: PRT
<213> ORGANISM: Homo sapiens

<400> SEQUENCE: 6

Leu Arg Thr Glu Gly Asp Gly Val Tyr Thr Leu Asn Asp Lys
1               5                   10

<210> SEQ ID NO 7
<211> LENGTH: 15
<212> TYPE: PRT
<213> ORGANISM: Homo sapiens

<400> SEQUENCE: 7

Leu Arg Thr Glu Gly Asp Gly Val Tyr Thr Leu Asn Asn Glu Lys
1               5                   10                  15

<210> SEQ ID NO 8
<211> LENGTH: 17
<212> TYPE: PRT
<213> ORGANISM: Homo Sapien

<400> SEQUENCE: 8

Ala Val Gly Asp Lys Leu Pro Glu Cys Glu Ala Val Cys Gly Lys Pro
1               5                   10                  15

Lys
```